(12) United States Patent
Seow et al.

(10) Patent No.: US 12,426,970 B2
(45) Date of Patent: Sep. 30, 2025

(54) ROBOTIC SURGICAL ASSEMBLIES

(71) Applicant: Covidien LP, Mansfield, MA (US)

(72) Inventors: Chi Min Seow, Watertown, MA (US); Michael A. Zemlok, Prospect, CT (US); Mark H. MacLeod, Brookfield, CT (US); Ranjan K. Mishra, Orange, CT (US); Eric J. Taylor, Southington, CT (US)

(73) Assignee: Covidien LP, Mansfield, MA (US)

( * ) Notice: Subject to any disclaimer, the term of this patent is extended or adjusted under 35 U.S.C. 154(b) by 900 days.

(21) Appl. No.: 17/671,784

(22) Filed: Feb. 15, 2022

(65) Prior Publication Data

US 2022/0168056 A1 Jun. 2, 2022

Related U.S. Application Data

(63) Continuation-in-part of application No. 17/466,358, filed on Sep. 3, 2021, now Pat. No. 11,896,332, which
(Continued)

(51) Int. Cl.
*A61B 34/37* (2016.01)
*A61B 17/29* (2006.01)
(Continued)

(52) U.S. Cl.
CPC .............. *A61B 34/37* (2016.02); *A61B 17/29* (2013.01); *A61B 34/30* (2016.02); *A61B 50/20* (2016.02);
(Continued)

(58) Field of Classification Search
CPC ......... A61B 50/20; A61B 90/50; A61B 34/30; A61B 34/37; A61B 34/71;
(Continued)

(56) References Cited

U.S. PATENT DOCUMENTS

| 5,460,062 A | 10/1995 | Wilson, Jr. |
| 6,923,613 B2 | 8/2005 | Stuyt |

(Continued)

FOREIGN PATENT DOCUMENTS

| WO | 2012104785 A1 | 8/2012 |
| WO | 2013159933 A1 | 10/2013 |
| WO | 2015167808 A1 | 11/2015 |

OTHER PUBLICATIONS

European Office Action dated Mar. 22, 2023 corresponding to counterpart Patent Application EP 17 753 648.9.
(Continued)

*Primary Examiner* — Martin T Ton
(74) *Attorney, Agent, or Firm* — Carter, DeLuca & Farrell LLP

(57) ABSTRACT

A surgical robotic assembly includes an instrument drive unit including a housing defining a longitudinal channel, a plurality of motors for performing functions of a surgical instrument, and a designated motor for rotating the instrument drive unit and the surgical instrument when the surgical instrument is attached to the instrument drive unit. The instrument drive unit allows for a top-loading or a side-loading of the surgical instrument thereto.

18 Claims, 14 Drawing Sheets

Related U.S. Application Data is a continuation of application No. 16/073,474, filed as application No. PCT/US2017/016769 on Feb. 7, 2017, now Pat. No. 11,109,926.

(60) Provisional application No. 62/295,815, filed on Feb. 16, 2016.

(51) Int. Cl.
*A61B 34/30* (2016.01)
*A61B 50/20* (2016.01)
*A61B 90/50* (2016.01)
*A61B 17/00* (2006.01)

(52) U.S. Cl.
CPC .... *A61B 90/50* (2016.02); *A61B 2017/00398* (2013.01); *A61B 2017/00477* (2013.01)

(58) Field of Classification Search
CPC .. A61B 2017/004477; A61B 2034/301; A61B 2034/302; A61B 2034/303
See application file for complete search history.

(56) References Cited

U.S. PATENT DOCUMENTS

| | | |
|---|---|---|
| 6,991,627 B2 | 1/2006 | Madhani et al. |
| 7,204,844 B2 | 4/2007 | Jensen et al. |
| 8,828,023 B2 | 9/2014 | Neff et al. |
| 11,109,926 B2 | 9/2021 | Seow et al. |
| 2002/0087166 A1 | 7/2002 | Brock et al. |
| 2008/0134841 A1 | 6/2008 | Wilson |
| 2010/0318101 A1 | 12/2010 | Choi |
| 2012/0116416 A1 | 5/2012 | Neff et al. |
| 2013/0123783 A1 | 5/2013 | Marczyk et al. |
| 2015/0073339 A1 | 3/2015 | Pacheco et al. |
| 2015/0090057 A1 | 4/2015 | Pacheco et al. |
| 2015/0327938 A1 | 11/2015 | Bencteux et al. |
| 2017/0049519 A1 | 2/2017 | Grover et al. |
| 2021/0022815 A1* | 1/2021 | Abbott ............... A61B 34/70 |
| 2021/0322116 A1* | 10/2021 | Swayze ............... B25J 9/102 |
| 2022/0022978 A1* | 1/2022 | Kapadia ............... A61B 34/30 |
| 2022/0096066 A1* | 3/2022 | Beckman ............... A61B 17/00 |
| 2022/0125528 A1* | 4/2022 | Li ............... A61B 34/30 |

OTHER PUBLICATIONS

European Search Report dated Feb. 22, 2018, corresponding to European Application No. 15785563.6; 7 pages.
International Search Report dated Jul. 9, 2015, corresponding to International Application No. PCT/US2015/026057; 4 pages.
European Search Report dated Oct. 7, 2019, corresponding to European Application No. 17753648.9; 10 pages.
Chinese Office Action with English translation, dated Jul. 13, 2020, corresponding to counterpart Chinese Application No. 201780009941.3; 19 total pages.
Chinese Office Action dated Mar. 2, 2021, issued in corresponding Chinese Appln. No. 201780009941, 8 pages.

* cited by examiner

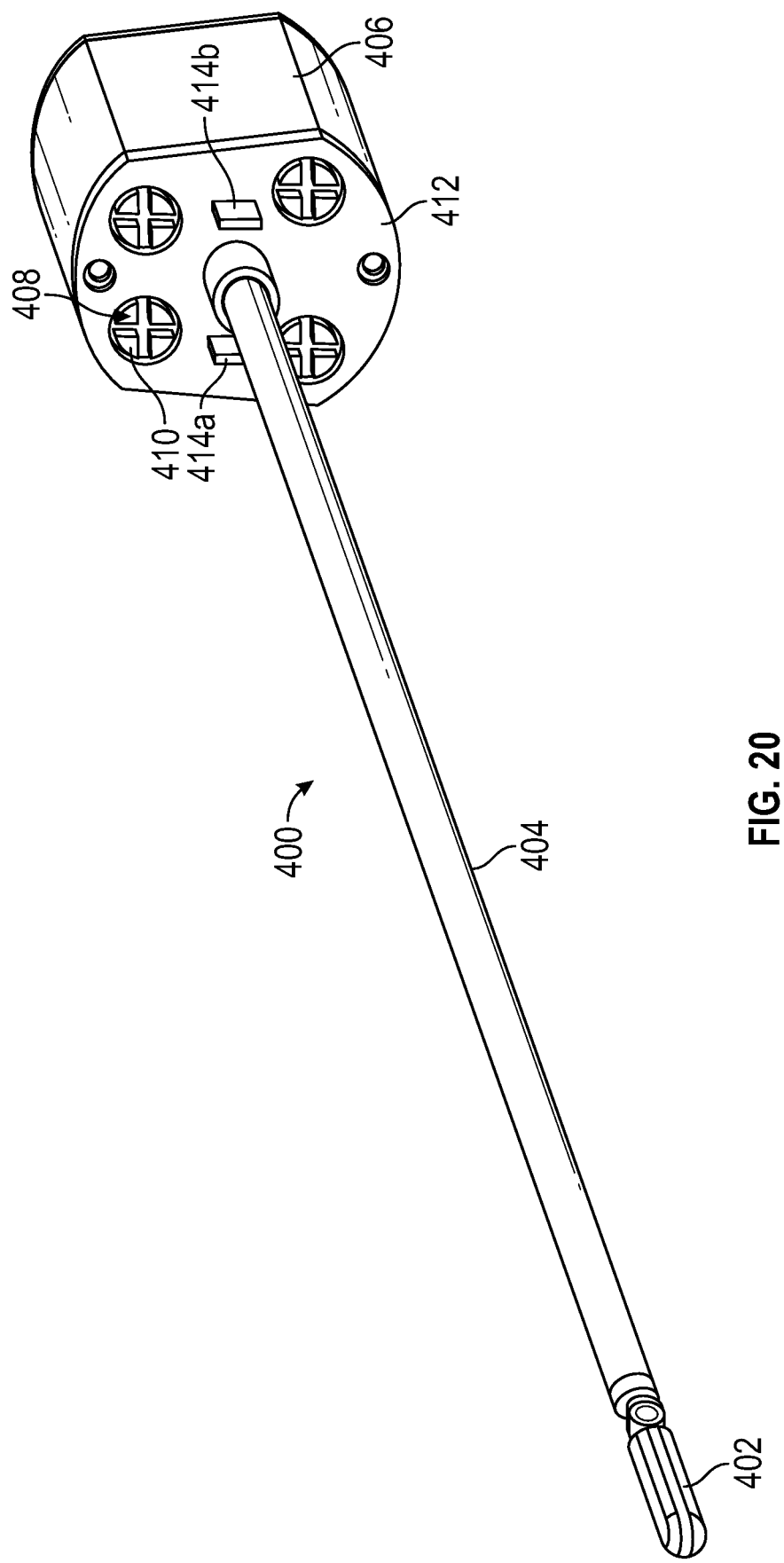

ROBOTIC SURGICAL ASSEMBLIES

BACKGROUND

Robotic surgical systems have been used in minimally invasive medical procedures. Some robotic surgical systems include a console supporting a surgical robotic arm and a surgical instrument, having at least one end effector (e.g., forceps or a grasping tool), mounted to the robotic arm. The robotic arm provides mechanical power to the surgical instrument for its operation and movement.

Manually-operated surgical instruments often include a handle assembly for actuating the functions of the surgical instrument. However, when using a robotic surgical system, no handle assembly is typically present to actuate the functions of the end effector. Accordingly, to use each unique surgical instrument with a robotic surgical system, an instrument drive unit is used to interface with the selected surgical instrument to drive operations of the surgical instrument. In robotic surgical systems, a robot arm may be used to hold the surgical instrument. In some robotic surgical systems, the entire length of the elongate shaft of the surgical instrument must pass through a holder or other feature of the robot arm, thereby making the removal or exchange of the surgical instrument cumbersome.

SUMMARY

In accordance with an aspect of the disclosure, a surgical robotic assembly is provided that includes a carriage configured for movable engagement to a surgical robotic arm, and an instrument drive unit. The carriage has a gear non-rotationally fixed thereto, and the instrument drive unit includes a housing rotatably supported on the carriage, a plurality of drive motors supported in the housing, and a rotation motor. The housing defines a longitudinal channel configured for passage of a shaft of a surgical instrument. The drive motors are positioned about the longitudinal channel and each has a rotatable drive coupler extending proximally from the respective drive motor. The drive couplers are configured to interface with a corresponding driven member of the surgical instrument. The rotation motor has a rotatable coupler configured to be operably coupled to the gear of the carriage such that rotation of the rotatable coupler of the rotation motor rotates the instrument drive unit, including the housing, the drive motors, and the rotation motor thereof, about a longitudinal axis of the instrument drive unit relative to the carriage.

In aspects, the gear of the carriage may be a ring gear, and the rotatable coupler of the rotation motor may be a pinion gear in meshing engagement with the ring gear.

In aspects, the instrument drive unit may include an annular guide non-rotationally fixed to the housing of the instrument drive unit and positioned about the longitudinal channel outwardly of the drive motors. The carriage may have a bearing interfacing with the annular guide.

In aspects, the housing of the instrument drive unit may define a lateral slot extending along a length of the housing and in communication with the longitudinal channel.

In aspects, the carriage may include a spine configured for slidable engagement with the surgical robotic arm, and a platform extending laterally from the spine and configured to support the housing of the instrument drive unit thereon.

In aspects, the surgical robotic assembly may further include a sterile interface module that includes a barrier, a plurality of couplers supported by the barrier, and a tubular shaft extending distally from the barrier. The barrier may be rotatably supported on the platform and non-rotationally fixed to the housing of the instrument drive unit. Each coupler may be configured to non-rotatably couple the respective driven member of the surgical instrument to the drive coupler of the instrument drive unit. The tubular shaft may extend through the longitudinal channel of the instrument drive unit.

In aspects, the tubular shaft may be a collapsible sheath configured to collapse from a first length to a second, reduced length.

In aspects, the housing of the instrument drive unit may have an outer surface defining a plurality of longitudinal grooves configured to dissipate heat from the drive motors.

In aspects, the instrument drive unit may include a slip ring assembly coupled to a proximal end portion of the housing of the instrument drive unit. The carriage may include an electrical contact in wiping contact with the slip ring assembly to transfer communication signals and/or power thereto.

In accordance with another aspect of the disclosure, a surgical robotic assembly is provided that includes an instrument drive unit and a sterile interface module. The instrument drive unit includes a housing, a plurality of drive motors supported in the housing, and a rotation motor. The housing defines a longitudinal channel configured for passage of a shaft of a surgical instrument, and a lateral slot extending alongside the longitudinal channel and in communication with the longitudinal channel. The drive motors are positioned about the longitudinal channel and each has a rotatable drive coupler configured to interface with a corresponding driven member of the surgical instrument. The rotation motor has a rotatable gear, and the instrument drive unit, including the housing, the drive motors, and the rotation motor, are configured to rotate about a longitudinal axis of the instrument drive unit in response to a rotation of the rotatable gear. The sterile interface module includes a barrier non-rotationally fixed to the housing of the instrument drive unit, a plurality of couplers rotatably supported by the barrier, and a tubular shaft extending distally from the barrier. The couplers of the sterile interface module are configured to non-rotatably couple the respective driven member of the surgical instrument to the respective drive coupler of the instrument drive unit. The tubular shaft is configured to extend through the longitudinal channel of the instrument drive unit and for passage of the shaft of the surgical instrument.

In aspects, the instrument drive unit may include an annular guide non-rotationally fixed to the housing of the instrument drive unit and positioned about the longitudinal channel outwardly of the drive motors.

In aspects, the housing of the instrument drive unit may have an outer surface defining a plurality of longitudinal grooves configured to dissipate heat from the drive motors.

In aspects, the instrument drive unit may include a slip ring assembly coupled to a proximal end portion of the housing of the instrument drive unit.

In accordance with further aspects of the disclosure, a surgical robotic assembly is provided that includes a surgical instrument and an instrument drive unit. The surgical instrument includes a housing, and a shaft extending distally from the housing. A plurality of driven members are rotatably supported in the housing. Each of the driven members have a driven coupler positioned at a distal end of the housing. The instrument drive unit includes a housing configured to support the housing of the surgical instrument thereon, and a plurality of drive motors supported in the housing of the instrument drive unit. The housing of the instrument drive unit defines a longitudinal channel configured for passage of the shaft of the surgical instrument. The drive motors are positioned about the longitudinal channel and each has a rotatable drive coupler positioned at a proximal end of the instrument drive unit and configured to interface with the respective driven coupler of the surgical instrument. The instrument drive unit, including the housing and the drive motors thereof, are configured to rotate about a longitudinal axis of the instrument drive unit to rotate the surgical instrument about a longitudinal axis of the surgical instrument.

In aspects, the instrument drive unit may include a rotation motor having a rotatable coupler. The instrument drive unit and the surgical instrument may be configured to rotate about the respective longitudinal axes thereof in response to a rotation of the rotatable coupler.

In aspects, the surgical robotic assembly may further include a carriage configured for movable engagement to a surgical robotic arm. The carriage may have a gear non-rotationally fixed thereto and configured for operable engagement with the rotatable coupler.

In aspects, the gear of the carriage may be a ring gear, and the rotatable coupler of the rotation motor may be a pinion gear in meshing engagement with the ring gear.

In aspects, the carriage may include a spine configured for slidable engagement with a surgical robotic arm, and a platform extending laterally from the spine and configured to rotatably support the housing of the surgical instrument and the housing of the instrument drive unit.

In aspects, the instrument drive unit may include an annular guide non-rotationally fixed to the housing of the instrument drive unit and positioned about the longitudinal channel outwardly of the drive motors. The carriage may have a bearing interfacing with the annular guide.

Further details and aspects of exemplary aspects of the disclosure are described in more detail below with reference to the appended figures.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Aspects of the disclosure are described herein with reference to the accompanying drawings, wherein:

FIG. 20 is a bottom, perspective view illustrating the surgical instrument of the surgical robotic assembly of FIG. 10.

DETAILED DESCRIPTION

Figure 1:
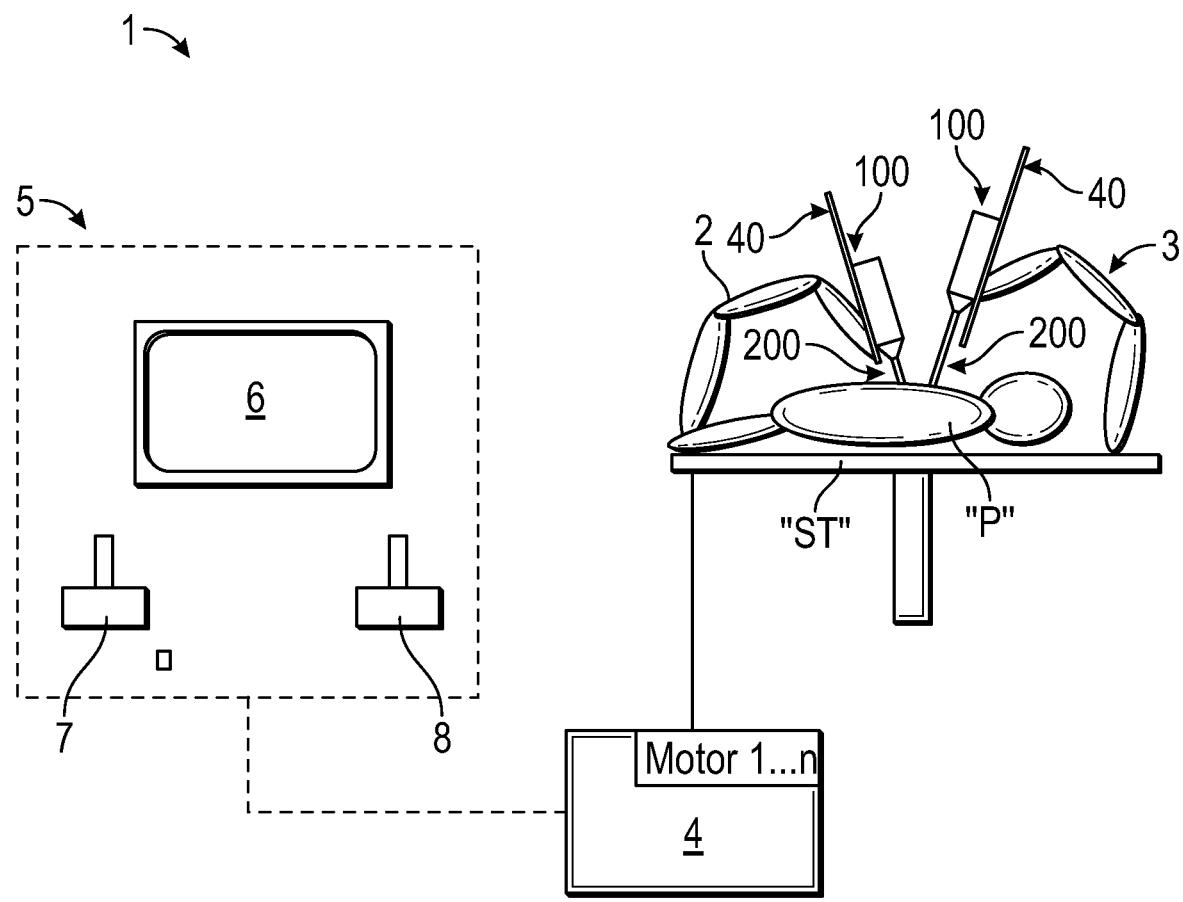
FIG. 1 is a schematic illustration of a robotic surgical system including a robotic surgical assembly in accordance with the disclosure.

Aspects of the disclosed surgical robotic assembly including an instrument drive unit, surgical instrument, sterile interface module, and surgical instrument holder, and methods thereof, are described in detail with reference to the drawings, in which like reference numerals designate identical or corresponding elements in each of the several views. As used herein the term "distal" refers to that portion of the assembly that is closer to the patient, while the term "proximal" refers to that portion of the assembly that is farther from the patient.

Robotic surgical instruments sometimes require actuators to drive a mechanism responsible for changing a yaw, pitch, and roll of the surgical instrument in addition to operating various functions of the surgical instrument. Similarly, an instrument drive unit may be needed for specialized robotic surgical instruments, such as, for example, clip appliers, surgical staplers, or more advanced power instruments. In aspects, an instrument drive unit may have a decoupled roll motion independent of the attached surgical instruments. Accordingly, the instrument drive unit typically has two sub-assemblies, a motor pack that has a set of actuators, which provides motion for changing the yaw, pitch, and jaw positions of the surgical instrument, and one sub assembly that provides rotation to the motor pack to which the instrument is attached.

The instrument drive unit allows bottom loading (e.g., in a proximal direction) or attaching of instruments through a sterile interface module. Bottom loading/unloading of instruments requires complete removal of the instrument from the port or trocar by sliding the instrument drive unit along a Z-slide distally away from the port. This method of loading/unloading is difficult for the bed side support staff due to lack of reachability and accessibility.

Accordingly, the disclosure enables top-loading (in a distal direction) and/or side-loading of surgical instruments into the instrument drive unit. For example, the instrument drive unit of the disclosure includes one roll-pitch-yaw power pack assembly and one bearing-slip ring assembly. The power pack assembly holds all drive actuators, including the instrument roll, torque sensors for the instrument drive actuators, and electronics for motor drive and sensor data amplifiers. The bearing-slip ring assembly has an open toroidal bearing arrangement, an open internal gear, and an open dual brush type gang slip ring.

Referring initially to FIG. 1, a surgical system, such as, for example, a robotic surgical system 1, generally includes a plurality of surgical robotic arms 2, 3 having a robotic surgical assembly 100 including an electromechanical surgical instrument 200 removably attached to a slide rail 40 of surgical robotic arms 2, 3; a control device 4; and an operating console 5 coupled with control device 4.

Operating console 5 includes a display device 6, which is set up in particular to display three-dimensional images; and manual input devices 7, 8, by means of which a person (not shown), for example a surgeon, is able to telemanipulate robotic arms 2, 3 in a first operating mode, as known in principle to a person skilled in the art. Each of the robotic arms 2, 3 may be composed of a plurality of members, which are connected through joints. Robotic arms 2, 3 may be driven by electric drives (not shown) that are connected to control device 4. Control device 4 (e.g., a computer) is set up to activate the drives, in particular by means of a computer program, in such a way that robotic arms 2, 3, the attached robotic surgical assembly 100, and thus electromechanical surgical instrument 200 (including an electromechanical end effector 210 (FIG. 2)) execute a desired movement according to a movement defined by means of manual input devices 7, 8. Control device 4 may also be set up in such a way that it regulates the movement of robotic arms 2, 3 and/or of the drives.

Robotic surgical system 1 is configured for use on a patient "P" lying on a surgical table "ST" to be treated in a minimally invasive manner by means of a surgical instrument, e.g., electromechanical surgical instrument 200. Robotic surgical system 1 may also include more than two robotic arms 2, 3, the additional robotic arms likewise being connected to control device 4 and being telemanipulatable by means of operating console 5. A surgical instrument, for example, electromechanical surgical instrument 200 (including the electromechanical end effector 210 (FIG. 2)), may also be attached to the additional robotic arm.

Control device 4 may control a plurality of motors, e.g., motors (Motor 1 . . . n), with each motor configured to drive movement of robotic arms 2, 3 in a plurality of directions. Further, control device 4 may control a plurality of motors (not shown) of an instrument drive unit 110 of robotic surgical assembly 100 that drive various operations of end effector 210 (FIG. 2) of electromechanical surgical instrument 200, and a rotation motor, such as, for example, a canister motor 112 (FIG. 2), configured to drive a relative rotation of electromechanical surgical instrument 200 along a longitudinal axis "X" (FIG. 2) thereof, as will be described in detail below. In aspects, each motor of the instrument drive unit 110 can be configured to actuate a drive rod/cable or a lever arm to effect operation and/or movement of the electromechanical end effector 210 of electromechanical surgical instrument 200.

For a detailed discussion of the construction and operation of a robotic surgical system, reference may be made to U.S. Pat. No. 8,828,023, filed on Nov. 3, 2011, entitled "Medical Workstation," the entire contents of which are incorporated by reference herein.

Figure 2:
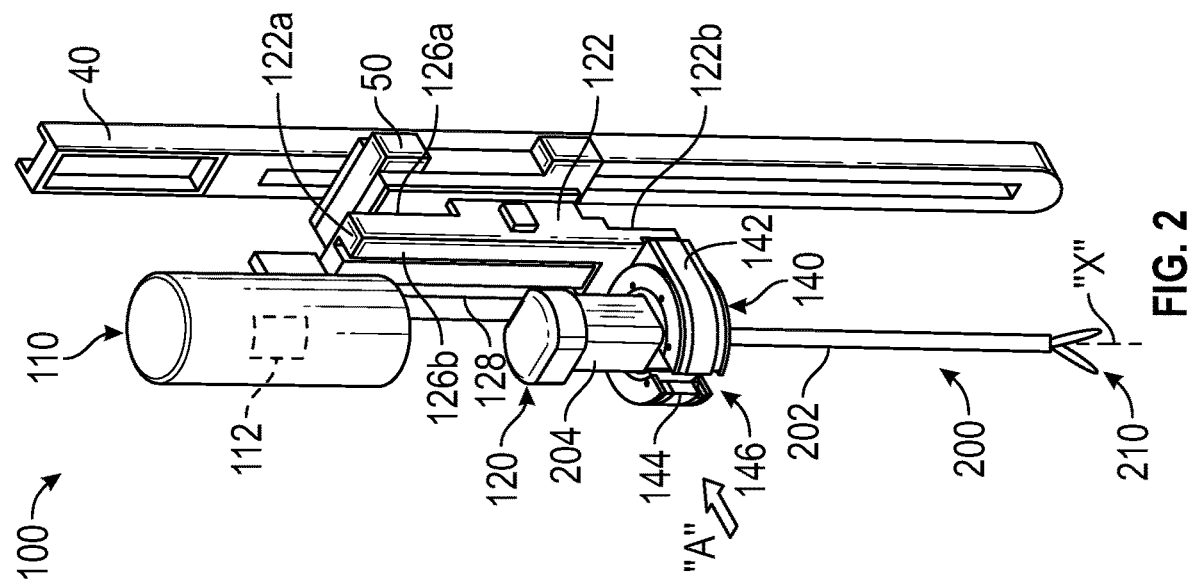
FIG. 2 is a perspective view, with parts separated, of the surgical assembly of FIG. 1.

With reference to FIGS. 1 and 2, robotic surgical system 1 includes the robotic surgical assembly 100 that is coupled with or to robotic arm 2 or 3. The robotic surgical assembly 100 includes instrument drive unit 110, a surgical instrument holder 120, and the electromechanical surgical instrument 200. Instrument drive unit 110 transfers power and actuation forces from its motors to driven members of electromechanical surgical instrument 200 to ultimately drive movement of components of the end effector 210 of electromechanical surgical instrument 200, for example, a movement of a knife blade (not shown) and/or a closing and opening of jaw members of the end effector 210, the actuation or firing of a stapler, and/or the activation or firing of an electrosurgical energy-based instrument, or the like. Instrument drive unit 110 is further configured to rotate electromechanical surgical instrument 200 about its longitudinal axis "X" by motor 112 (e.g., a fifth axis rotation motor) of instrument drive unit 110.

Turning now to FIGS. 2-6, surgical instrument holder 120 of surgical assembly includes a back member or carriage 122 and a drive coupler 140 extending perpendicularly from an end 122b of carriage 122. In some aspects, drive coupler 140 may extend at various angles relative to carriage 122 and from various portions of carriage 122. Carriage 122 has a first side 126a and a second side 126b, opposite first side 126a. First side 126a of carriage 122 may be detachably connectable to a slide 50, which is slidably mountable to rail 40 of robotic arm 2. Alternately, first side 126a of carriage 122 may be permanently mounted with range/displacement limits. Second side 126b of carriage 122 defines a longitudinal track 128 configured for slidable receipt of instrument drive unit 110. Carriage 122 may support or house a motor (not shown) which receives controls and power from control device 4 to selectively move instrument drive unit 110 along longitudinal track 128. Carriage 122 has a rotatable shaft 130 (FIG. 5) extending longitudinally therethrough for interconnecting fifth motor 112 of instrument drive unit 110 to a plurality of inter-related gears 132, 170a, 170b, 164 (FIG. 6) in drive coupler 140 to effect a rotation of surgical instrument 200 about its longitudinal axis "X," as will be described in greater detail below. Alternatively, rotation motor 112 may be mechanically coupled to one of gears 132, 170a, or 170b in drive coupler 140.

Figure 3:
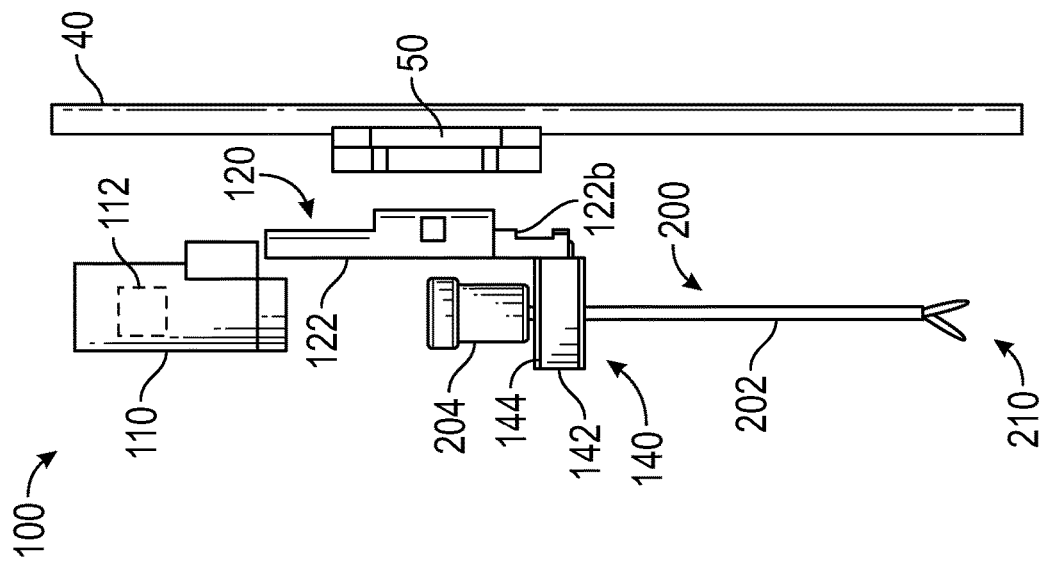
FIG. 3 is a side view of the surgical assembly of FIG. 2.

With reference to FIGS. 2 and 3, drive coupler 140 of surgical instrument holder 120 is configured to receive and hold surgical instrument 200 and effect rotation of surgical instrument 200 about its longitudinal axis "X," as will be described in detail below. Drive coupler 140 generally includes a C-shaped outer member 142 and an inner member 144 rotatably disposed within outer member 142. In some aspects, outer member 142 may have features for positional clocking and may assume a variety of shapes, such as, for example, V-shaped, hook-shaped, or an asymmetrical form. Outer member 142 includes a pair of arms each having an arcuate configuration. The arms each include a first end 142a fixedly engaged to end 122b of carriage 122, and a second free end 142b. Second ends 142b of the arms are spaced from one another to define a lateral slot 146 of outer member 142 configured for lateral receipt of a shaft 202 of surgical instrument 200. As such, surgical instrument 200 can be positioned within drive coupler 140 of surgical instrument holder 120 by moving surgical instrument 200 in a direction perpendicular to its longitudinal axis "X" and through lateral slot 146 of outer member 142.

Figure 5:
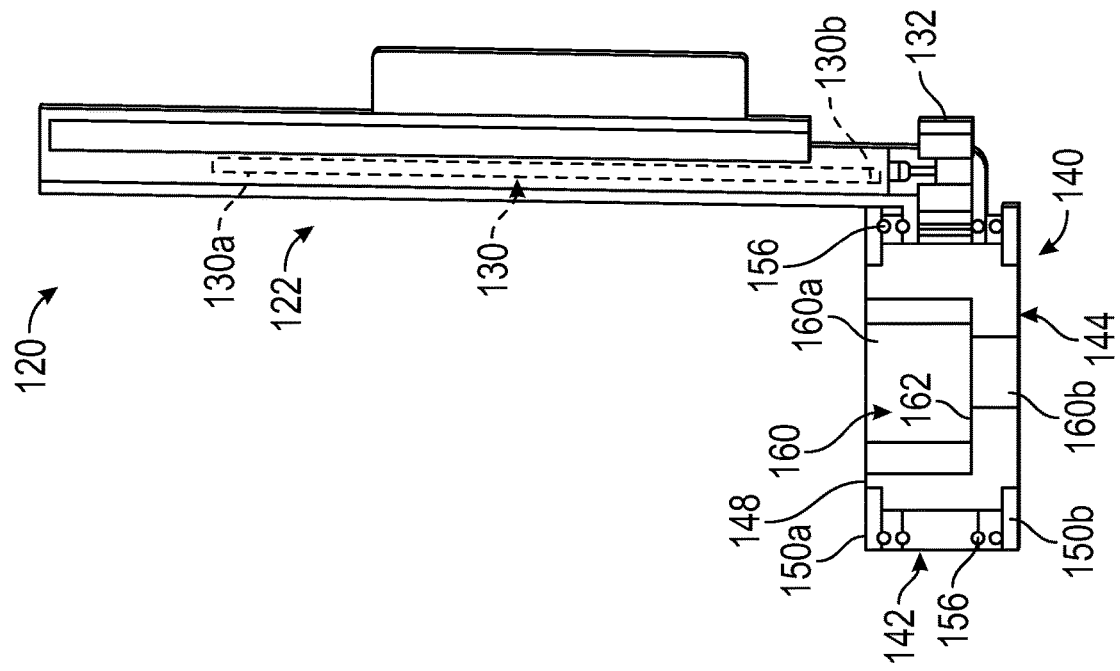
FIG. 5 is a cross sectional view, taken along line 5-5 in FIG. 4, of the surgical instrument holder.
Figure 4:
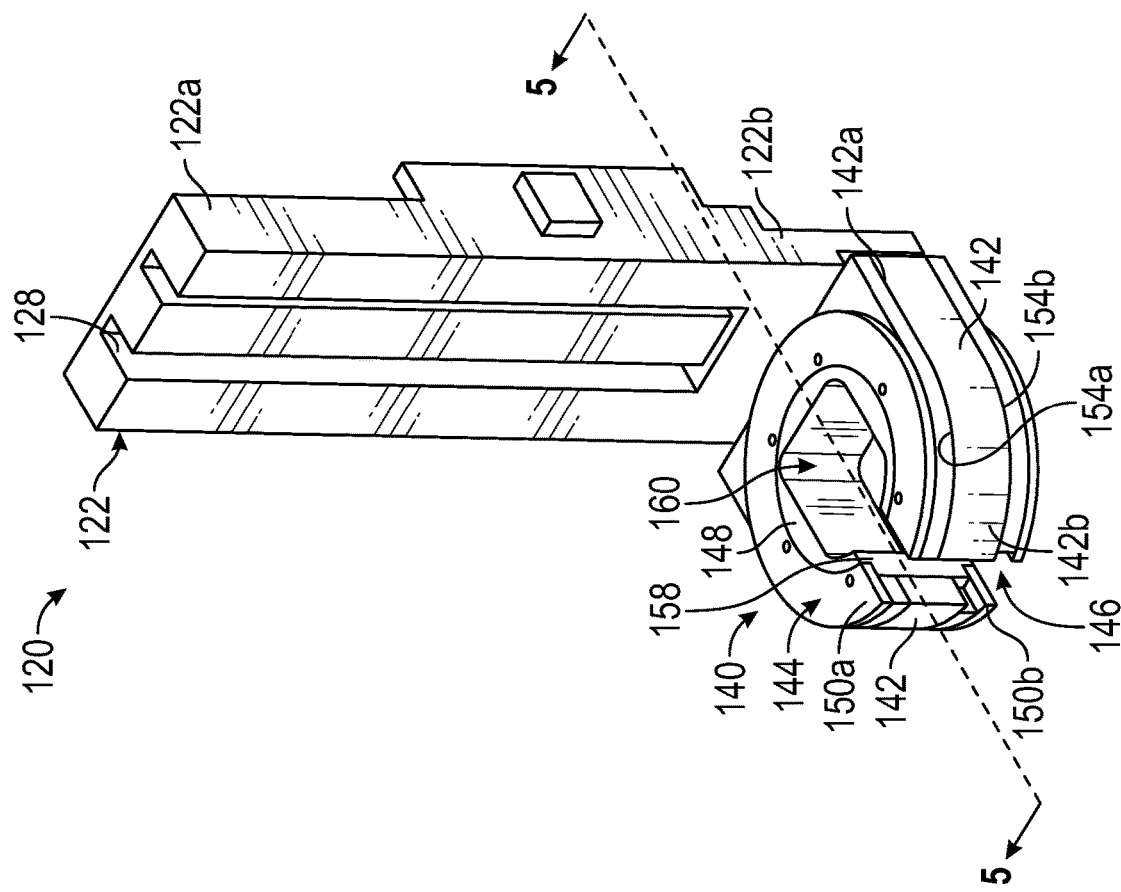
FIG. 4 is a perspective view of a surgical instrument holder of the surgical assembly of FIG. 2.

With reference to FIGS. 4 and 5, inner member 144 of drive coupler 140 of surgical instrument holder 120 is configured to hold surgical instrument 200 and to cause surgical instrument 200 to rotate therewith. Inner member 144 includes an internal housing 148 and upper and lower plates 150a, 150b fixed to opposing sides of internal housing 148. Upper and lower plates 150a, 150b each have a c-shaped configuration and are supported on, or abut, an upper surface 154a and a lower surface 154b of outer member 142, respectively. Plates 150a, 150b of inner member 144 maintain internal housing 148 of inner member 144 within outer member 142 while permitting rotation of inner member 144 relative to outer member 142. A plurality of bearings 156, such as, for example, a split bushing or a recirculating ball bearing that has a split in the middle, are disposed between upper plate 150a of inner member 144 and upper surface 154a of outer member 142, and lower plate 150b of inner member 144 and lower surface 154b of outer member 142, to facilitate rotation of inner member 144 relative to outer member 142.

In some aspects, upper and lower bearing journals or races (not shown) can be incorporated into inner member 144 to axially and radially support inner member 144, and which may be fabricated from any combination of metals, ceramics, or plastics.

Internal housing 148 of inner member 144 defines a lateral slot 158 therein for lateral passage of shaft 202 of surgical instrument 200 therethrough. Lateral slot 158 of inner member 144 has the same or substantially the same dimensions (e.g., width) as lateral slot 146 of outer member 142. As such, inner member 144 can be rotated relative to outer member 142 to a position in which lateral slot 158 of inner member 144 and lateral slot 146 of outer member 142 are in alignment. When lateral slots 146, 158 are in alignment, surgical instrument 200 can be laterally loaded into surgical instrument holder 120 or laterally unloaded from surgical instrument holder 120.

With specific reference to FIG. 5, internal housing 148 of inner member 144 further defines a counterbore 160 therein configured for receipt of housing 204 of surgical instrument 200 therein. Counterbore 160 includes a first cavity 160a and a second cavity 160b in communication with first cavity 160a. A bottom internal surface 162 of internal housing 148 that defines first cavity 160a of counterbore 160 is configured to support or seat housing 204 of surgical instrument 200 thereon when surgical instrument 200 is disposed within drive coupler 140 of surgical instrument holder 120. First cavity 160a of counterbore 160 has a non-circular configuration or profile (e.g., squared or D-shaped) corresponding to a non-circular outer configuration or profile of housing 204 of surgical instrument 200. In some aspects, first cavity 160a of counterbore 160 may be round with clocking, or may be asymmetrical. In some aspects, the depth of counterbore 160 of inner member 144 may be low to minimize the axial displacement required for loading and unloading of surgical instrument 200.

Upon seating housing 204 of surgical instrument 200 within first cavity 160a of counterbore 160, rotation of inner member 144 results in rotation of surgical instrument 200 since housing 204 of surgical instrument 200 is non-rotatably captured within first cavity 160a of counterbore 160. In some aspects, housing 204 of surgical instrument 200 and first cavity 160a of counterbore 160 may be circular, and housing 204 of surgical instrument 200 may be non-rotatably disposed within first cavity 160a via a friction fit engagement or other various engagements.

Second cavity 160b of counterbore 160 is narrower than first cavity 160a and is configured for receipt of shaft 202 of surgical instrument 200. Second cavity 160b of counterbore 160 is in communication with lateral slot 158 of inner member 144 such that shaft 202 of surgical instrument 200 can be laterally received within second cavity 160b of counterbore 160 by being passed through lateral slot 158 of internal housing 148 of inner member 144.

In some aspects, the motor that drives the rotation of inner member 144 may be local to inner member 144 or it may be displaced using a drive shaft, a flex shaft, or a belt. In some aspects, the motor that drives the rotation of inner member 144 can incorporate mechanical or electrical brakes or a high back drive mechanism such as a worm drive for desired back drive torques or positional locking for critical modes of operation.

Figure 6:
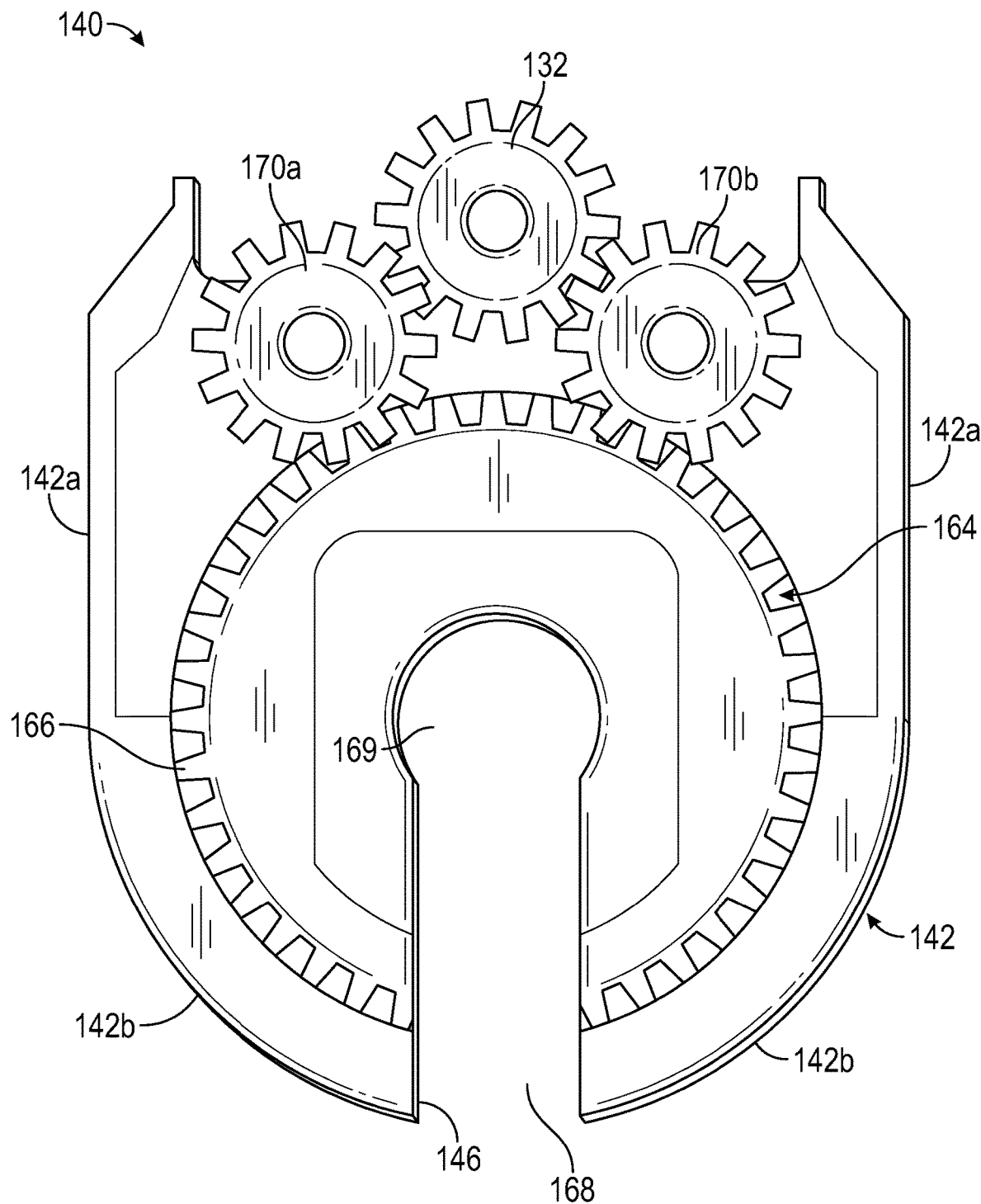
FIG. 6 is a top view, with parts removed, of a drive coupler of the surgical instrument holder of FIG. 4 illustrating a lateral slot of a first gear in alignment with a lateral slot of an outer member of the surgical instrument holder.

With reference to FIGS. 4-6, inner member 144 of drive coupler 140 further includes a first gear 164 embedded within (i.e., in non-rotatable engagement with) internal housing 148 of inner member 144 such that internal housing 148 of inner member 144 rotates with first gear 164 of inner member 144. First gear 164 has an annular shape and a plurality of gear teeth 166 extending radially from a periphery thereof. First gear 164 defines a lateral slot 168 therein, which is in fixed alignment with lateral slot 158 of inner member 144. First gear 164 further defines a central passageway 169, e.g., a circular passageway, extending therethrough in communication with lateral slot 168 of first gear 164. Upon seating surgical instrument 200 within inner member 144 of drive coupler 140, shaft 202 of surgical instrument 200 extends through passageway 169 of first gear 164. First gear 164 is in operable association with shaft 130 of carriage 122, which is driven by rotation motor 112, such that rotation of shaft 130 rotates first gear 164 to rotate inner member 144 relative to outer member 142, as will be described in greater detail below.

With specific reference to FIG. 6, drive coupler 140 of surgical instrument holder 120 further includes a pair of gears 170a, 170b, such as, for example, spur gears, disposed adjacent second end 122b of carriage 122 (FIG. 4). Both gears 170a, 170b are in meshing engagement with teeth 166 of first gear 164 to transfer rotational motion from a second gear 132 of shaft 130 to first gear 164. Gears 170a, 170b are spaced from one another a distance greater than the width of lateral slot 168 of first gear 164. Specifically, a point of engagement of gears 170a, 170b with first gear 164 is spaced from one another by a distance greater than an arcuate distance or length of lateral slot 168 of first gear 164 along an outer radial edge of first gear 164. In this way, as first gear 164 rotates within outer member 142 to a position in which lateral slot 168 of first gear 164 is radially aligned with one of gears 170a, 170b, or in any position relative to gears 170a, 170b, at least one of gears 170a, 170b will be in contact with first gear 164 such that the transfer of rotational motion from gears 170a, 170b to first gear 164 will be uninterrupted.

In some aspects, gears 132, 170a, 170b, 164 of drive coupler 140, or any gear disclosed herein, may be spur gears, bevel gears, or miter gears, and may incorporate a helix or spiral profile to minimize noise and backlash.

In some aspects, instead of having the pair of gears 170a, 170b, drive coupler 140 may be configured such that second gear 132 of shaft 130 may be in direct meshing engagement with first gear 164. In this aspect, second gear 132 of shaft 130 has a diameter whereby an arc length of second gear 132 spans across the width of lateral slot 168 of first gear 164 so that second gear 132 always remains in contact with at least one tooth of first gear 164 irrespective of the position of first gear 164 relative to second gear 132.

In some aspects, gear 164, or any suitable component of inner member 144, may incorporate an encoder, a magnet, a ferrous-containing optical target that can be read by a corresponding sensor element (not shown) of slide 50. In some aspects, gear 164, or any suitable component of inner member 144, may incorporate controls and/or firmware. When robotic surgical assembly 100 is in an initialization mode or in an instrument exchange mode, the controls and/or firmware may move gear 164, or any component of inner member 144, to position lateral slot 168 of gear 164 and/or lateral slot 158 of inner member 144 out of alignment with or perpendicular to lateral slot 146 of outer member 142.

As briefly mentioned above with respect to FIG. 5, surgical instrument holder 120 has a shaft 130 extending longitudinally through carriage 122 to operably interconnect the fifth motor 112 or an additional motor of instrument drive unit 110 and first gear 164 of drive coupler 140 of surgical instrument holder 120. Shaft 130 of surgical instrument holder 120 has a first end 130a configured to operably connect to motor 112 of instrument drive unit 110, and a second 130b end having second gear 132 non-rotatably disposed thereabout. As such, an actuation of motor 112 of instrument drive unit 110 effects rotation of shaft 130 and second gear 132 therewith. Rotation of second gear 132 rotates gears 170a, 170b, which in turn, rotates first gear 164 relative to and within outer member 142 of drive coupler 140.

In some aspects, shaft 130 of surgical instrument holder 120 may incorporate an encoder or a rotational position sensor configured to sense a rotational position of lateral slot 168 of first gear 164. In some aspects, the encoder may be disposed at any suitable location of surgical instrument holder 120. The encoder is readable to align first gear 164 of inner member 144 for any desired application and to confirm function. In some aspects, shaft 130 of surgical instrument holder 120, or any suitable component of surgical instrument holder 120, may incorporate a gearhead (not shown) to provide additional torque or back drive loads to gear 164.

In operation, prior to or during a surgical procedure, surgical instrument 200 may be coupled to robotic arm 2. In particular, instrument drive unit 110 may be moved, either manually or by actuating a motor within carriage 122 of surgical instrument holder 120, away from drive coupler 140 to a position toward a first end 122a of carriage 122, as shown in FIG. 2. The motor 112 of instrument drive unit 110 is actuated to drive rotation of shaft 130 of surgical instrument holder 120. Rotation of shaft 130 effects rotation of second gear 132, which is non-rotatably attached to second end 130b of shaft 130. Rotation of second gear 132, which is in meshing engagement with gears 170a, 170b, causes gears 170a, 170b to rotate. Rotation of gears 170a, 170b causes first gear 164 of drive coupler 140 to rotate relative to and within outer member 142. Actuation of the motor 112 of instrument drive unit 110 is continued until lateral slot 158 of inner member 144, and thus also lateral slot 168 of first gear 164, are in alignment with lateral slot 146 of outer member 142 to provide a pathway for shaft 202 of surgical instrument 200 to pass.

With instrument drive unit 110 spaced from drive coupler 140 of surgical instrument holder 120 and lateral slots 146, 168, 158 of drive coupler 140 in alignment with one another, surgical instrument 200 is moved in a lateral direction, as indicated by arrow "A" in FIG. 2, toward surgical instrument holder 120 to pass shaft 202 of surgical instrument 200 through lateral slots 146, 158 and into second cavity 160b of inner member 144 of drive coupler 140. Housing 204 of surgical instrument 200 may then be seated within first cavity 160a of inner member 144 of drive coupler 140 to non-rotatably dispose surgical instrument 200 with surgical instrument holder 120. Instrument drive unit 110 may then be translated toward housing 204 of surgical instrument 200 to operably couple drive couplers or sleeves (not shown) of instrument drive unit 110 with corresponding driven couplers or sleeves (not shown) of housing 204 of surgical instrument 200, and operably couple the motor(s) 112 of instrument drive unit 110 with surgical instrument 200.

With surgical instrument 200 disposed within surgical instrument holder 120 and operably connected to instrument drive unit 110, an actuation of a motor 112 of instrument drive unit 110 will rotate shaft 130 of surgical instrument holder 120 to rotate second gear 132. Rotation of second gear 132 results in a rotation of first gear 164 via gears 170a, 170b. As first gear 164 rotates, inner member 144 of drive coupler 140 rotates therewith and relative to outer member 142 to effect rotation of surgical instrument 200 about its longitudinal axis "X" and relative to surgical instrument holder 120. As such, a rotational position of end effector 210 of surgical instrument 200 may be selectively adjusted while surgical instrument 200 is held within surgical instrument holder 120.

Further, by having one of gears 170a, 170b in contact or in engagement with first gear 164 at all times, as first gear 164 is rotated and lateral slot 168 of first gear 164 radially aligns with gear 170a, gear 170b may continue to independently drive and rotate first gear 164. Likewise, when lateral slot 168 of first gear 164 radially aligns with gear 170b, gear 170a may continue to independently drive and rotate first gear 164. In this manner, first gear 164 (including lateral slot 168) may be rotated more than 360 degrees as needed to rotate surgical instrument 200 about its longitudinal axis "X."

To unload or remove surgical instrument 200 from surgical instrument holder 120, a motor 112 of instrument drive unit 110 is actuated to rotate inner member 144, including first gear 164, relative to outer member 142 until lateral slots 146, 168, 158 of drive coupler 140 are in alignment. Instrument drive unit 110 may then be translated away from housing 204 of surgical instrument 200 to disconnect surgical instrument 200 from instrument drive unit 110. With lateral slots 146, 168, 158 in alignment with one another and instrument drive unit 110 disconnected from surgical instrument 200, surgical instrument 200 can be removed from surgical instrument holder 120 by being moved laterally through lateral slots 146, 168, 158 and out of drive coupler 140 of surgical instrument holder 120.

Under certain circumstances in which power to instrument drive unit 110 is disrupted, surgical instrument 200 may be removed by manually moving instrument drive unit 110 away from housing 204 of surgical instrument 200 and surgical instrument 200 may be manually rotated until lateral slots 146, 168, 158 of drive coupler 140 are aligned with one another. Upon manually aligning lateral slots 146, 168, 158, surgical instrument 200 can be removed from surgical instrument holder 120 by being moved laterally through lateral slots 146, 168, 158 and out of drive coupler 140 of surgical instrument holder 120.

In some aspects, inner member 144, or any component thereof, may be sterilized through autoclave, use of an ethylene oxide (ETO) process, use of peroxide, use of gamma radiation or be aseptically covered with a sterilized upper and lower cover. Inner member 144 may be fabricated from various metals, for example, steel, aluminum, and/or magnesium alloy, and may incorporate platings or coatings to prolong cleanability and wear. Inner member 144 may be made from various plastics, polymers, and/or ceramics, and may include drafting and/or elastomer interference features to minimize play and movement when loaded.

Figure 7:
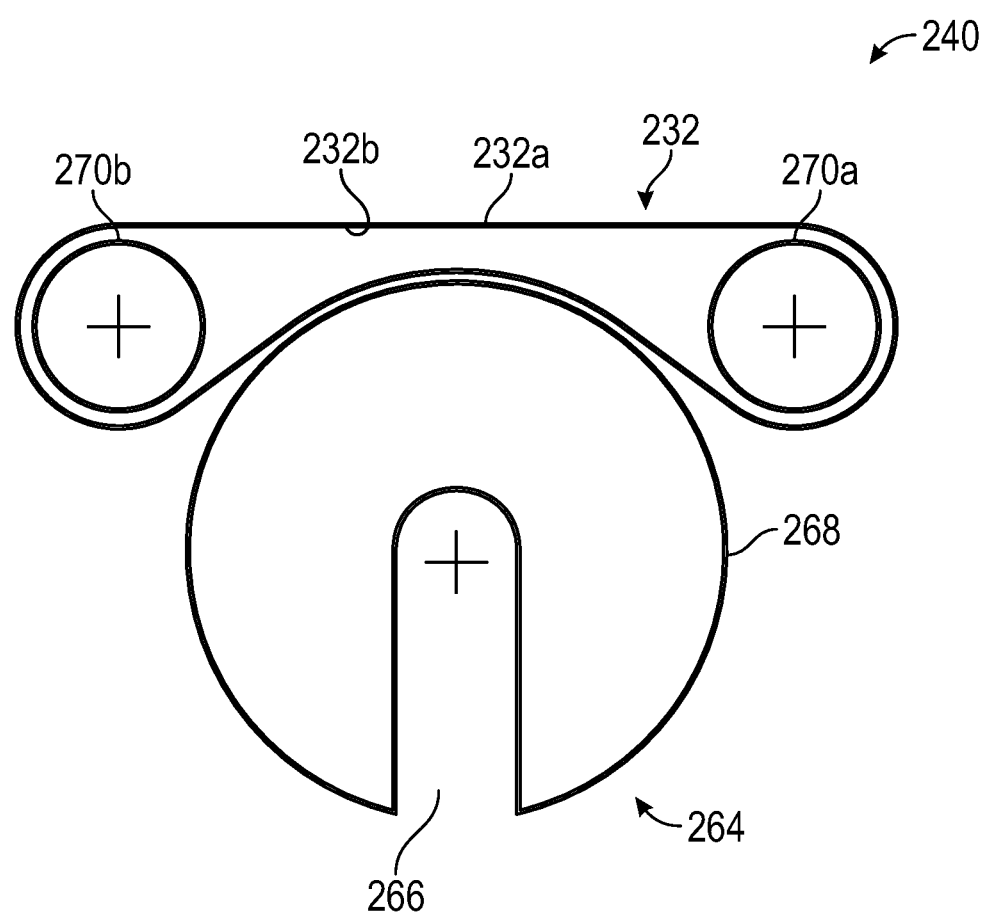
FIG. 7 is a top view of a pulley system configured to be incorporated into the surgical instrument holder of FIG. 4.

With reference to FIG. 7, another aspect of a drive coupler 240 is provided, similar to drive coupler 140 described above with reference to FIG. 6. Drive coupler 240 differs from drive coupler 140 by replacing the gears 164, 170*a*, 170*b*, 132 of drive coupler 140 with a pulley system, as will be described. The pulley system of drive coupler 240 includes an annular member or a cup 264, a driver pulley 270*a*, an idler pulley 270*b*, and a belt 232. Cup 264 is configured to receive surgical instrument 200 (FIG. 2) therein, and transfer its rotational motion to surgical instrument 200 when surgical instrument 200 is received therein. Cup 264 defines a lateral slot or slit 266 therein configured for the lateral passage of shaft 202 of surgical instrument 200.

In some aspects, cup 264 may act as a replacement for the gear 164 of drive coupler 140 (FIG. 5) and be incorporated into or embedded within internal housing 148 of inner member 144 (FIG. 5). In another aspect, cup 264 may act as a replacement for the internal housing 148 of inner member 144 (FIG. 5) and assume a similar shape as internal housing 148 of inner member 144.

Driver pulley 270*a* is configured to be non-rotatably coupled to shaft 130 (FIG. 5) of surgical instrument holder 120 such that rotation of shaft 130, via an actuation of motor 112 of instrument drive unit 110, rotates driver pulley 270*a*. Idler pulley 270*b* is spaced from driver pulley 270*a*, for example, a distance equal to or substantially equal to the diameter of cup 264. Belt 232 of the pulley system has an inner surface 232*a* wrapped around driver pulley 270*a* and idler pulley 270*b*, and an outer surface 232*b* in frictional or toothed engagement with an outer surface 268 of cup 264. As such, a rotation of driver pulley 270*a* causes drive belt 232 to rotate about pulleys 270*a*, 270*b* to effect a rotation of cup 264.

Figure 8:
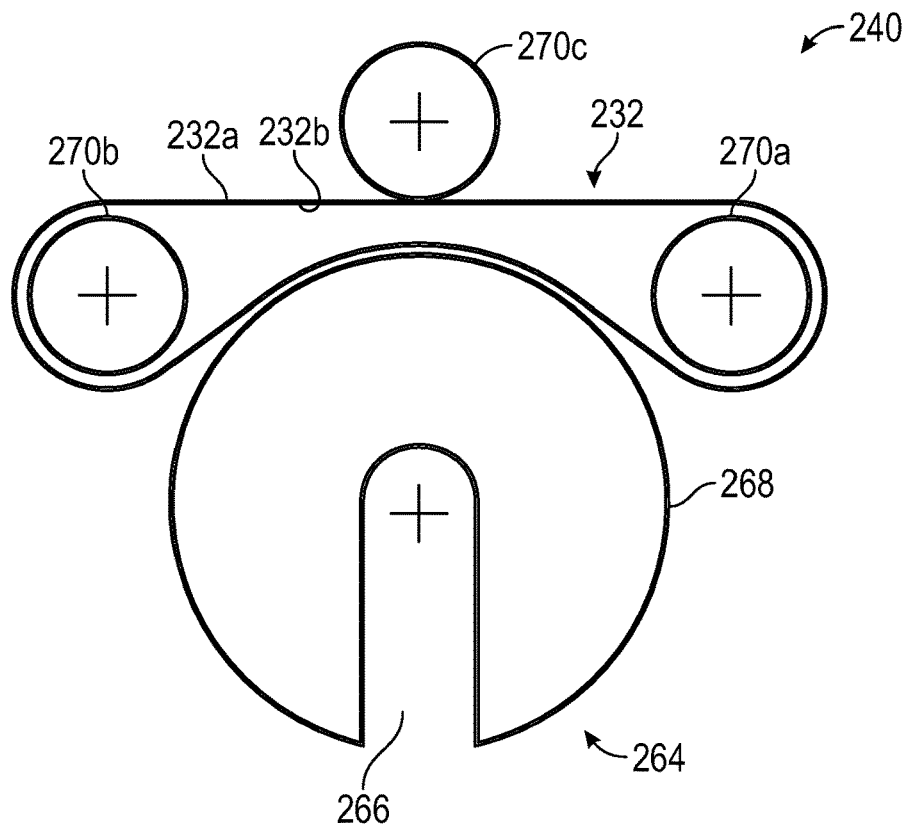
FIG. 8 is a top view of another aspect of a pulley system configured to be incorporated into the surgical instrument holder of FIG. 4.

With reference to FIG. 8, drive coupler 240 may include a second idler pulley 270*c* disposed at a location that is equidistant from driver pulley 270*a* and first idler pulley 270*b*. Second idler pulley 270*c* is engaged to outer surface 232*b* of belt 232 to add tension in belt 232. In some aspects, second idler pulley 270*c* may act as an additional driver pulley by being operably coupled to a drive shaft (not shown) of surgical instrument holder 120 to add torque to the pulley system.

Figure 9:
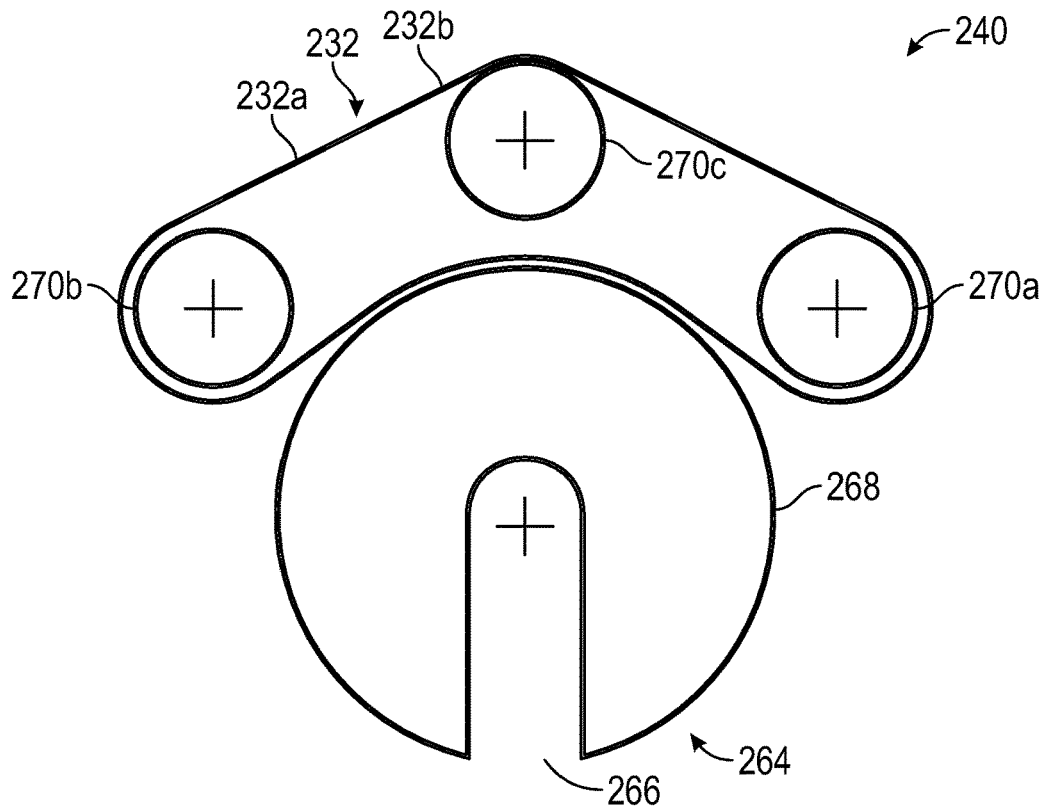
FIG. 9 is yet another aspect of a pulley system configured to be incorporated into the surgical instrument holder of FIG. 4.

With reference to FIG. 9, instead of second idler pulley 270*c* being disposed outside of belt 232, idler pulley 270*c* may be disposed within belt 232 and engaged to inner surface 232*a* of belt 232 to add tension in belt 232.

The pulley system of FIGS. 7-9 reduces noise, reduces backlash, and provides a lower profile or minimized form factor for the motor drive mechanism placement.

In some aspects, instrument drive unit 110, or any suitable component thereof, may include position sensors and/or encoders within its drives configured to auto-align and clock instrument drive unit 110 with gear 164 or any suitable component of inner member 144. In some aspects, instrument drive unit 110 may be mounted onto slide 50 with positions for instrument exchange or for different height or length instrument housings. Instrument drive unit 110 may also incorporate an additional pivot mount (not shown), or there may be a separate, removable device (not shown) that is loaded onto the top of surgical instrument 200 or to provide axial loading access. Instrument drive unit 110 may be sterilized through autoclave, use of an ethylene oxide (ETO) process, use of peroxide, use of gamma radiation or be aseptically placed in a sterilized housing cover or be under a sterile drape with a sterile interface plate. Instrument drive unit 110 can be powered with an external cable or with an internal connector interface.

FIGS. 10-20 depict another type of surgical robotic assembly 300 and components thereof, which is similar to and may include any of the features of surgical robotic assembly 100 (FIG. 1), except as explicitly contradicted below.

Figure 10:
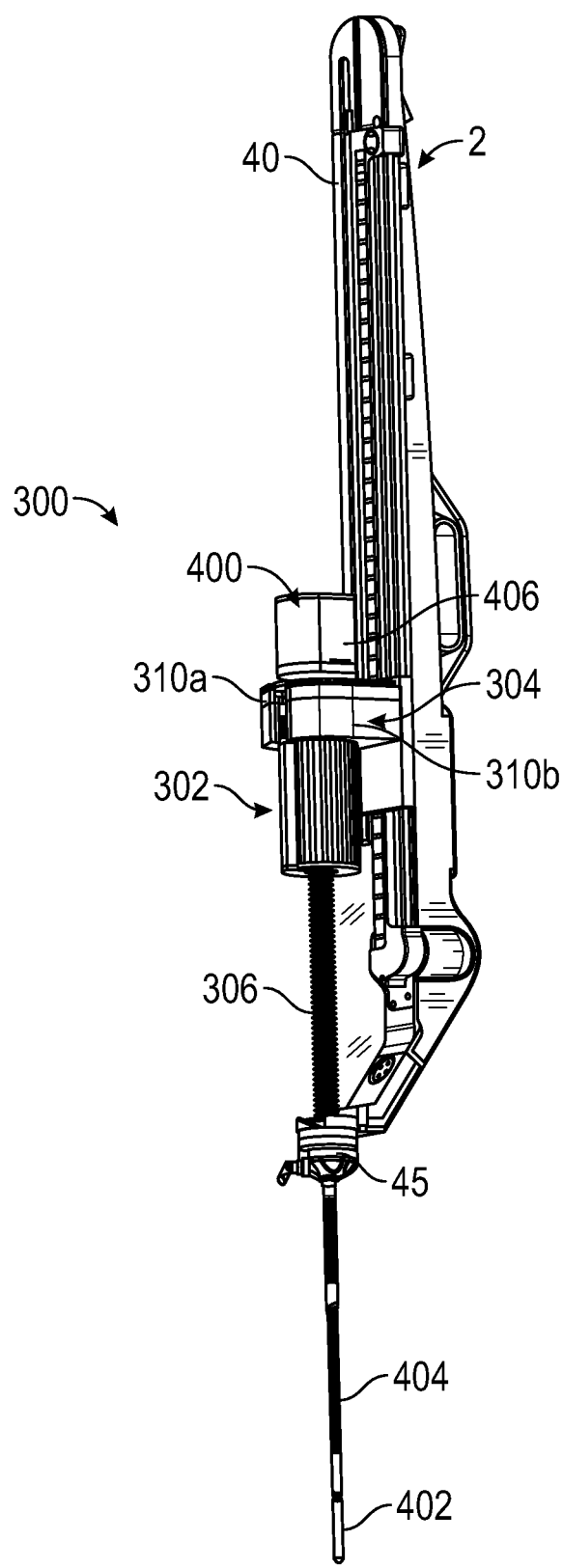
FIG. 10 is a perspective view illustrating a surgical robotic assembly including a carriage supported on a slide rail of a surgical robotic arm, an instrument drive unit supported on the carriage, a sterile interface module, and a surgical instrument.
Figure 11:
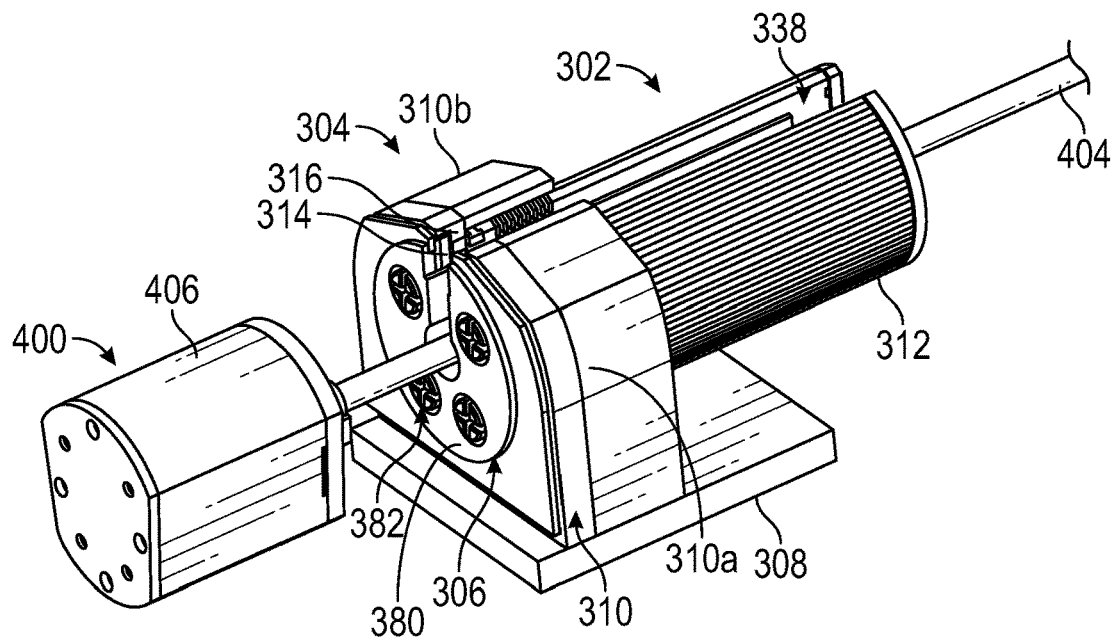
FIG. 11 is a perspective view illustrating the surgical instrument being top-loaded into the instrument drive unit and carriage of FIG. 10.

With reference to FIGS. 10 and 11, the surgical robotic assembly 300 is coupled with or to robotic arm 2 or 3 (FIGS. 1 and 10) and generally includes an instrument drive unit 302, a surgical instrument holder or carriage 304, a sterile interface module 306, and a surgical instrument 400. The instrument drive unit 302 transfers power and actuation forces from its motors to driven members 408 (FIG. 20) of the surgical instrument 400 to ultimately drive movement of components of an end effector 402 of the surgical instrument 400, for example, a movement of a knife blade (not shown) and/or a closing and opening of jaw members of the end effector 402, the actuation or firing of a stapler, and/or the activation or firing of an electrosurgical energy-based instrument, or the like. Instrument drive unit 302 is further configured to rotate relative to the carriage 304 and rotate the surgical instrument 400 therewith.

The carriage 304 of the surgical robotic assembly 300 includes a back member or spine 308, and a platform 310 extending laterally (e.g., perpendicularly) from the spine 308. The spine 308 is slidably coupled to a slide rail 40 (FIG. 10) of the surgical robotic arm 2 to adjust an axial position of the instrument drive unit 302 and the attached surgical instrument 400. The platform 310 may include a pair of hooked arms 310*a*, 310*b* configured to support a housing 312 of the instrument drive unit 302 such that the housing 312 of the instrument drive unit 302 is rotatable relative to and within the pair of arms 310*a*, 310*b* while being prohibited from moving axially relative to the pair of arms 310*a*, 310*b*. For example, a proximal end of the housing 312 of the instrument drive unit 302 may have a ledge 314 rotatably supported on a ledge 316 of the platform 310.

Figure 12:
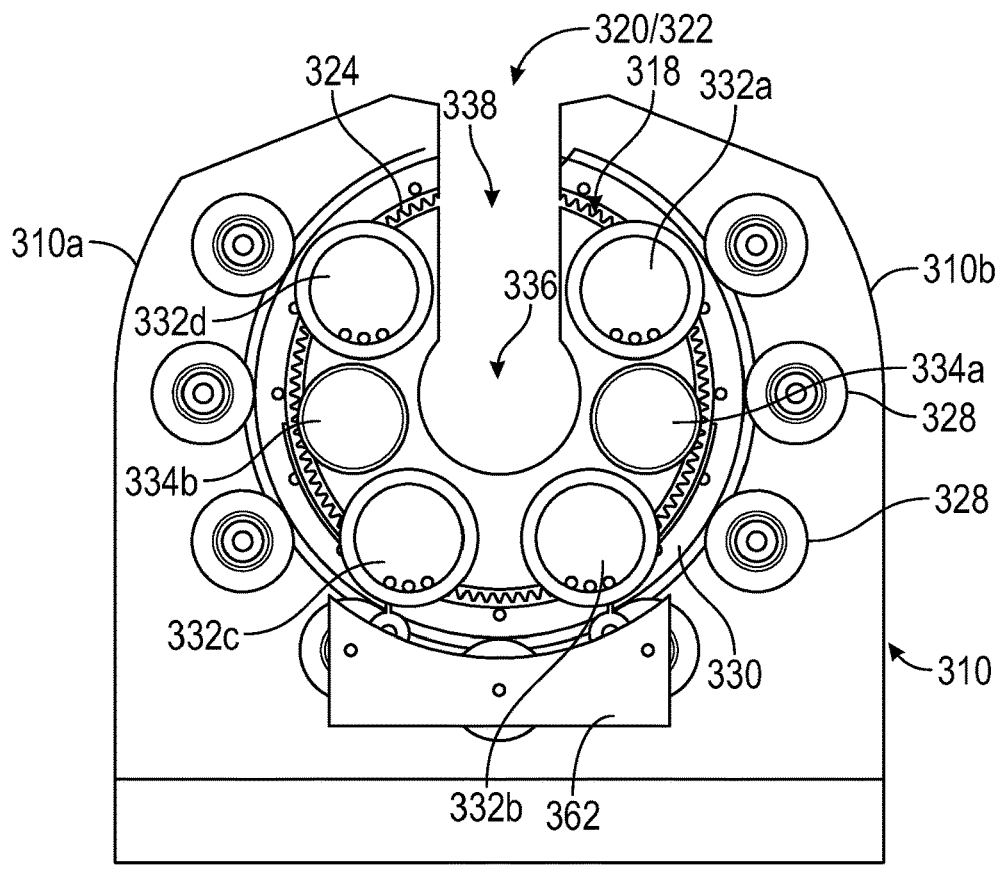
FIG. 12 is a bottom view illustrating internal components of the instrument drive unit and carriage of FIG. 10.
Figure 13:
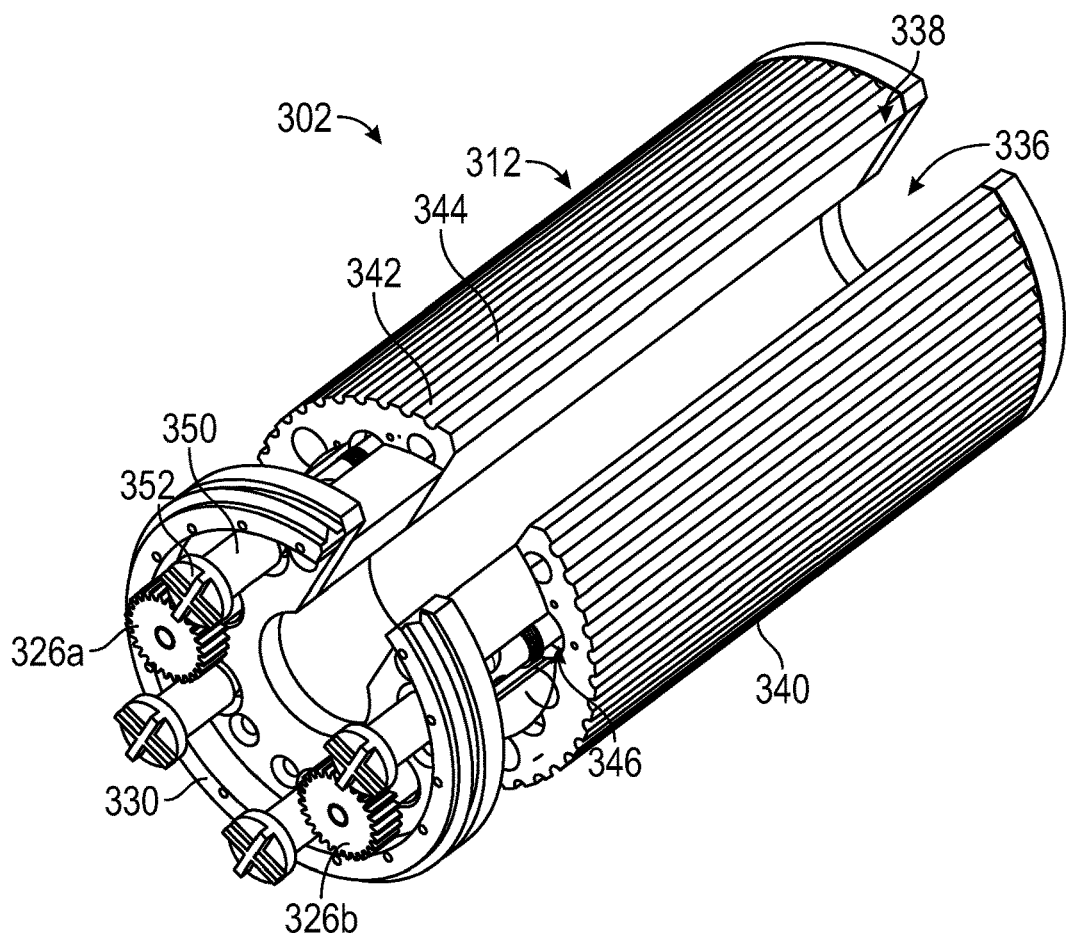
FIG. 13 is a perspective view, with parts removed, of the instrument drive unit of FIG. 10.
Figure 14:
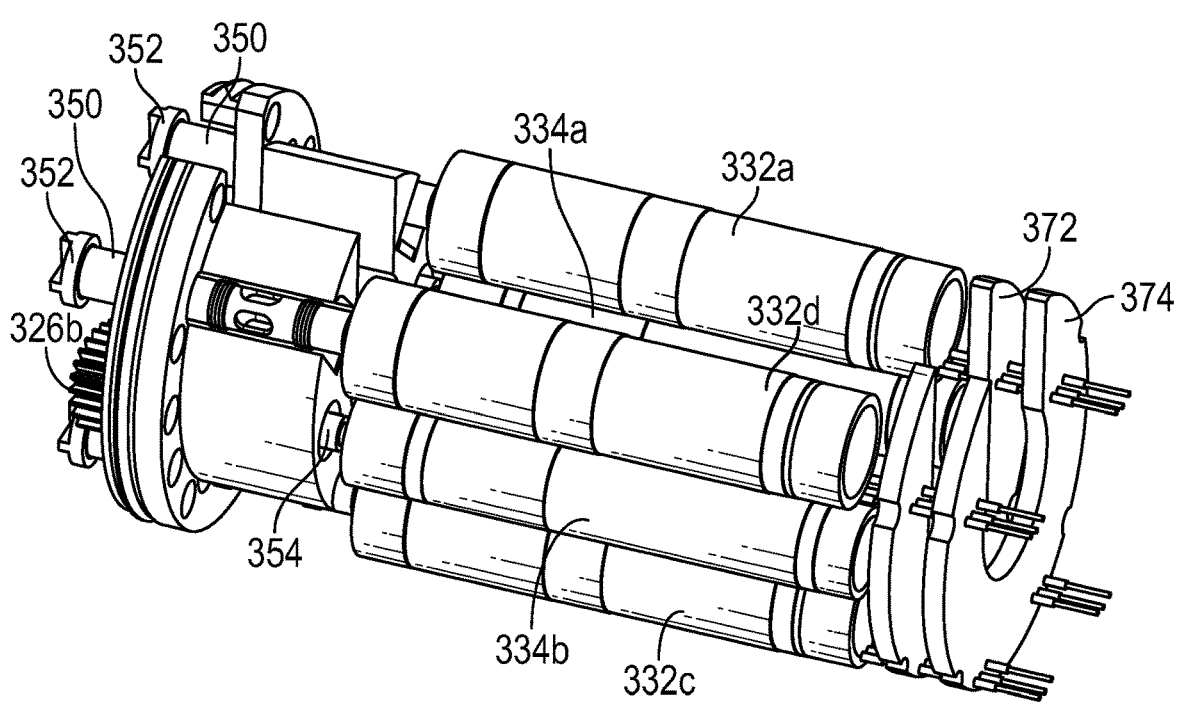
FIG. 14 is a perspective view of the instrument drive unit of FIG. 10 with an outer housing thereof removed to show internal components of the instrument drive unit.

With reference to FIG. 12, the carriage 304 further includes a ring gear 318 fixed within the platform 310 such that the instrument drive unit 302 is rotatable relative to the ring gear 318. The ring gear 318 defines a lateral slot 320 that is contiguous with an opening 322 defined between respective ends of the pair of arms 310*a*, 310*b* of the platform 310. The ring gear 318 has a plurality of teeth 324 projecting from an inner peripheral surface thereof configured for meshing engagement with a pair of couplers 326*a*, 326*b* (FIG. 13) of the instrument drive unit 302. In alternate aspects, the ring gear 318 may be non-rotationally coupled to the instrument drive unit 302.

A plurality of roller bearings 328 of the carriage 304 are rotatably supported in the platform 310 of the carriage 304 and surround the ring gear 318. The roller bearings 328 are configured for engagement with an annular bearing guide 330 of the instrument drive unit 302 for facilitating rotation of the instrument drive unit 302 relative to the carriage 304. Each of the roller bearings 328 may define a V-shaped notch 332 (FIG. 15) therein configured for receipt of a V-shaped protrusion 334 of the annular bearing guide 330 of the instrument drive unit 302. It is contemplated that the ring gear 318 of the carriage 304 may be positioned above (e.g., proximal) and in axial alignment with the annular bearing guide 330 of the instrument drive unit 302 with the teeth 324 of the ring gear 318 projecting inwardly relative to the annular bearing guide 330.

With reference to FIGS. 11-14, the instrument drive unit 302 includes the housing 312, a plurality of drive motors 332a, 332b, 332c, 332d (collectively referred to herein as drive motors 332), and a pair of rotation motors 334a, 334b. While the instrument drive unit 302 is depicted as having four drive motors 332, it is contemplated that the instrument drive unit 302 may have more or less than four drive motors 332.

The housing 312 of the instrument drive unit 302 may be a cylindrical body defining a central longitudinal channel 336 therethrough configured for passage of the shaft 404 of the surgical instrument 400, and a lateral slot 338 extending transversely through the housing 312 and along the length of the housing 312. The lateral slot 338 has a width (e.g., defined circumferentially about a portion of the housing 312) slightly larger than a diameter of the shaft 404 (FIG. 11) of the surgical instrument 400 such that the shaft 404 of the surgical instrument 400 may be side-loaded into central longitudinal channel 336 of the instrument drive unit 302 via the lateral slot 338.

The housing 312 of the instrument drive unit 302 may have an outer surface 340 defining a plurality of longitudinal grooves 342 and ridges 344 that together function as a heat sink for transferring heat generated by the motors 332, 334a, 334b to an external environment. Alternately or additionally, the grooves 342 and ridges 344 may be configured for engagement with a pulley drive system (not show) for rotating the housing 312. The housing 312 of the instrument drive unit 302 defines a plurality of longitudinal bores 346 (FIG. 13) positioned circumferentially around the central longitudinal channel 336 and each having a respective drive motor 332 or rotation motor 334 supported therein.

Each of the drive motors 332 of the instrument drive unit 302 has a drive shaft 350 extending proximally therefrom and configured to be rotatably driven by the respective drive motor 332. Each of the drive shafts 350 of the drive motors 332 has a drive coupler 352, such as, for example, a crosshead cavity or protrusion, configured for non-rotational coupling with a corresponding driven coupler 410 (FIG. 20) of the surgical instrument 400. The drive couplers 352 of the instrument drive unit 302 may assume any other suitable type of configuration configured to transfer rotational motion therefrom to the corresponding driven coupler 410 of the surgical instrument 400.

The rotation motors 334a, 334b of the instrument drive unit 302 each include a drive shaft 354 extending proximally therefrom and which are drivingly rotated by the rotation motors 334a, 334b. Each of the drive shafts 354 of the rotation motors 334a, 334b has a drive coupler 326a, 326b configured to operably engage the teeth 324 (FIG. 12) of the ring gear 318 of the carriage 302. For example, the drive couplers 326a, 326b may be pinion gears in meshing engagement with the ring gear 318 of the carriage 304 such that rotation of the drive couplers 326a, 326b of the rotation motors 334a, 334b rotate the entire instrument drive unit 302 relative to the carriage 304. The drive couplers 326a, 326b of the rotation motors 334a, 334b may be positioned at opposite sides of the central longitudinal channel 336 of the housing 312 of the instrument drive unit 302 so that at least one of the drive couplers 326a or 326b is engaged to ring gear 318 at any given rotational position of the instrument drive unit 302 relative to the carriage 304.

Figure 15:
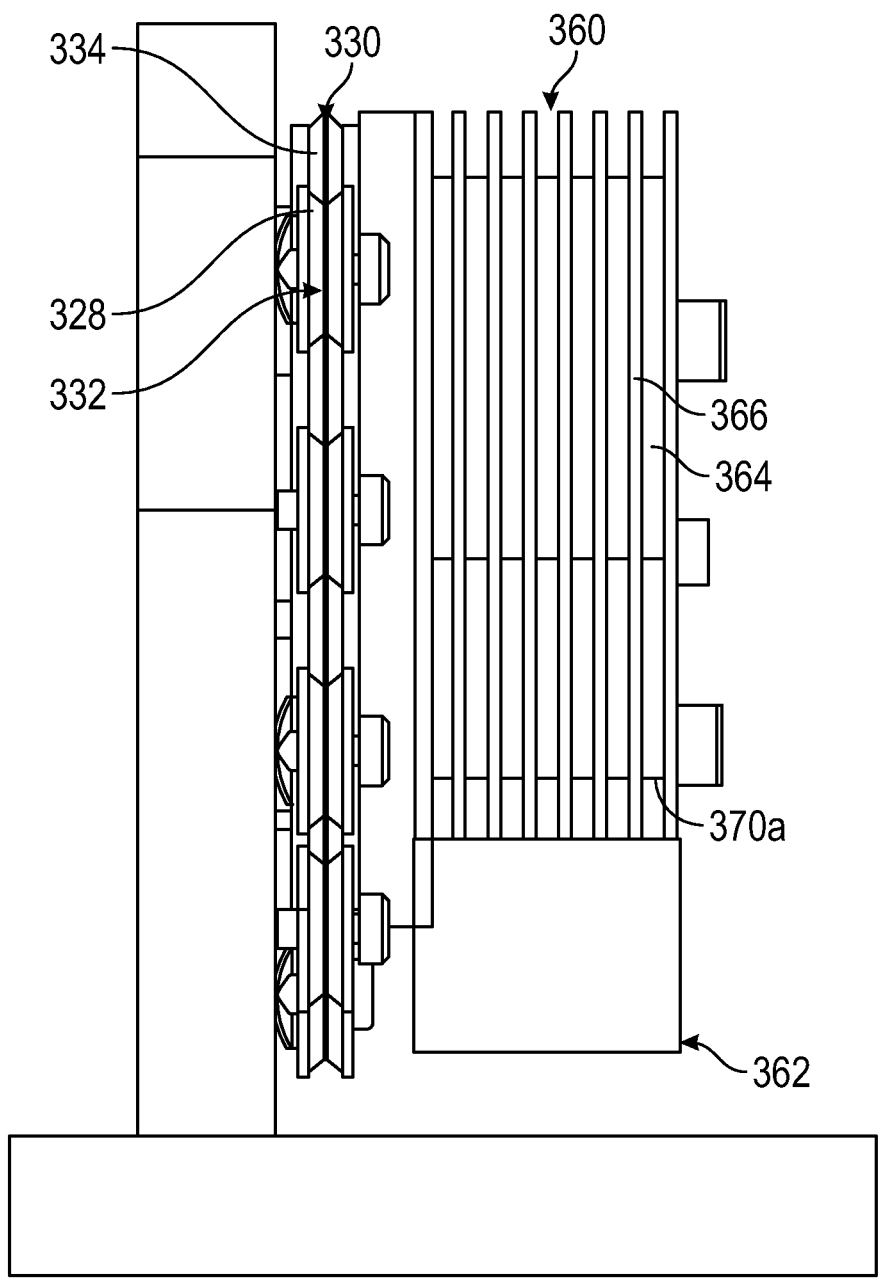
FIG. 15 is a side view illustrating a slip ring assembly of the instrument drive unit and a bearing assembly of the carriage.
Figure 16:
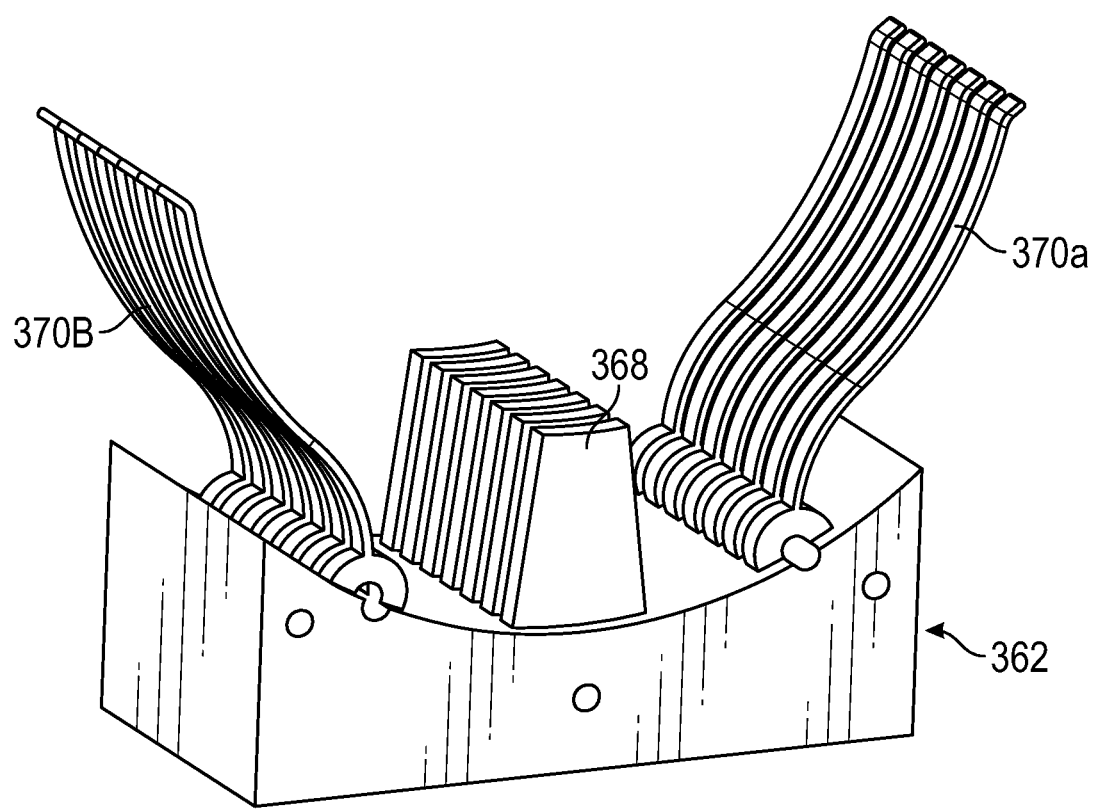
FIG. 16 is a perspective view illustrating an electrical contact of the carriage.

With reference to FIGS. 12, 15, and 16, the drive motors 332 of the instrument drive unit 302 are in electrical communication with the control device 4 (FIG. 1) by an electrical connection between a slip ring assembly 360 of the instrument drive unit 302 and an electrical contact 362 of the carriage 302. More specifically, the slip ring assembly 360 of the instrument drive unit 302 includes a plurality of contact rings 364 separated from one another via a plurality of partitions 366. Each of the contact rings 364 is in constant, sliding contact with corresponding replaceable wipers 368 of the electrical contact 362. The electrical contact 362 may further include a first set of brushes 370a in electrical contact with the corresponding contact rings 364, and a second set of brushes 370b in electrical contact with the corresponding contact rings 364. The wipers 368, together with the first and second set of brushes 370a, 370b ensure that the slip-ring assembly 360 maintains electrical communication with the electrical contact 362 throughout rotation of the instrument drive unit 302 relative to the carriage 304. The instrument drive unit 302 may include motor drive electronics 372 (FIG. 14) and torque sensor/etherCAT electronics 374 positioned at a distal end thereof and in communication with the drive motors 332.

Figure 17:
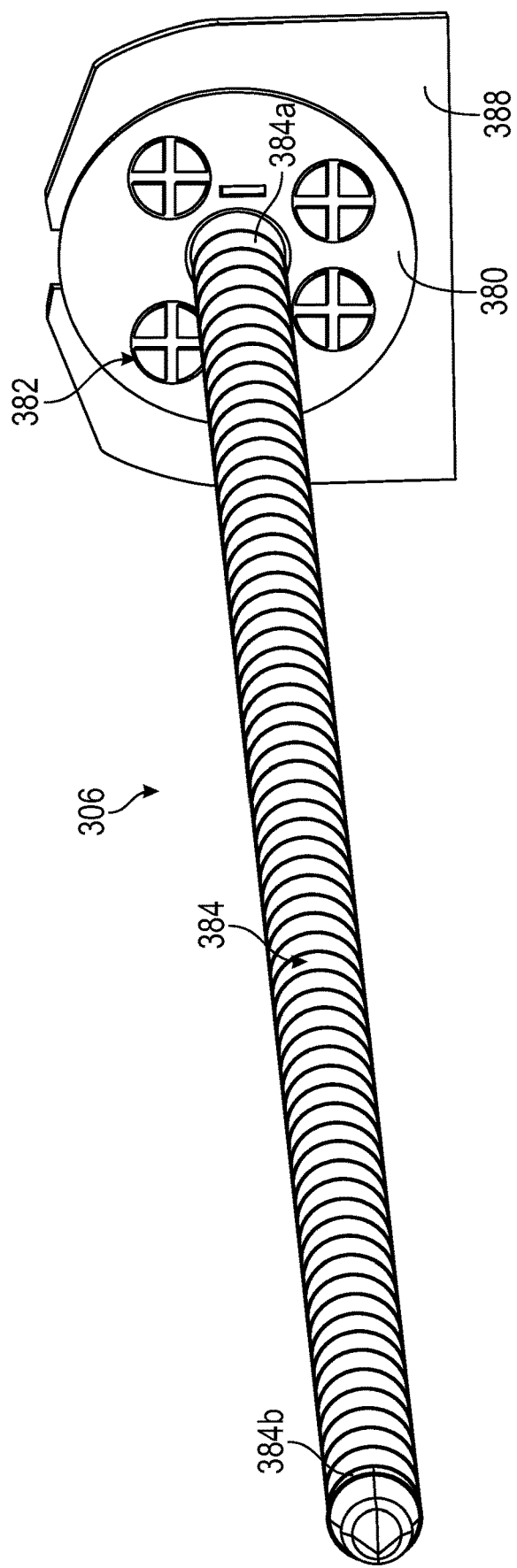
FIG. 17 is a perspective view illustrating the sterile interface module of the surgical robotic assembly of FIG. 10.
Figure 18:
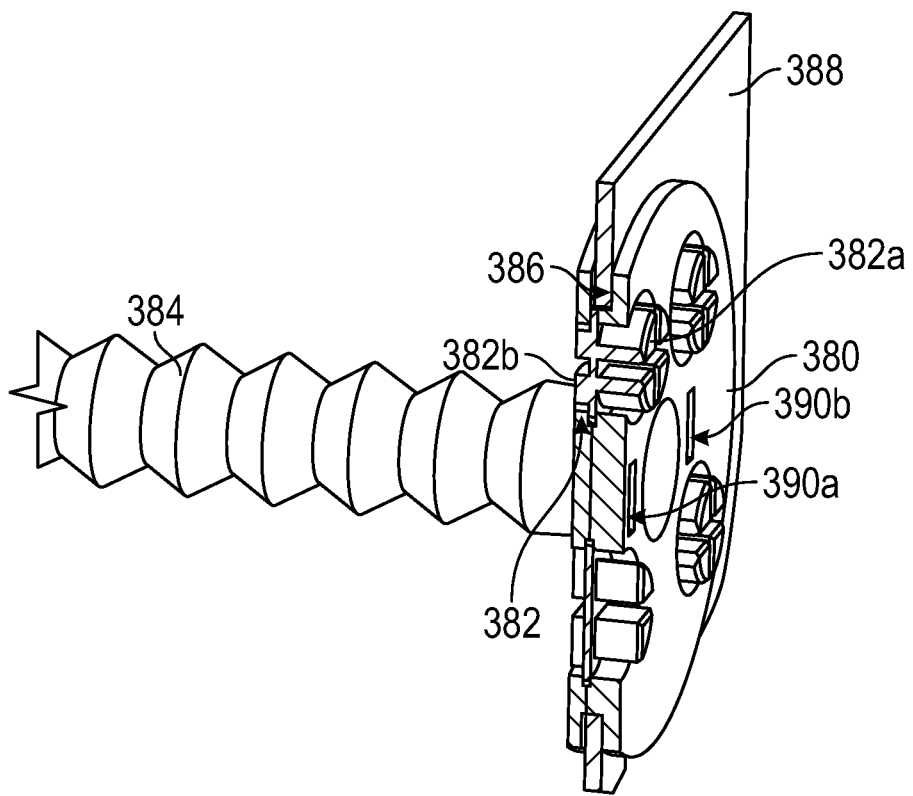
FIG. 18 is a partial cross-sectional view of the sterile interface module of FIG. 17.

With reference to FIGS. 11, 17, and 18, the sterile interface module 306 of the surgical robotic assembly 300 includes a barrier 380, such as, for example, a plate, rotatably supported on the platform 310 (FIG. 11) of the carriage 304, a plurality of couplers 382 rotatably supported within the barrier 380, and a tubular shaft 384 extending distally from a center of the barrier 380. The barrier 380 is configured to be non-rotationally fixed to the proximal end of the housing 312 of the instrument drive unit 302, and therefore rotatable therewith and relative to the carriage 304. In aspects, the barrier 380 may define an annular slot 386 in an outer periphery thereof configured to capture a surgical drape ring 388 therein. Each of the couplers 382 has a proximal end 382a exposed at a proximal side of the barrier 380, and a distal end 382b exposed at a distal side of the barrier 380. The proximal end 382a of the couplers 382 are configured to drivingly couple to the drive couplers 352 (FIG. 14) of the instrument drive unit 302 and the distal end 382b of the drive couplers 382 are configured to drivingly couple to the driven coupler 410 (FIG. 20) of the surgical instrument 40.

The tubular shaft 384 of the sterile interface module 305 may be a collapsible sheath configured for receipt of the shaft 404 of the surgical instrument 400. The tubular shaft 384 is configured to collapse from a fully extended length to a plurality of reduced lengths. The tubular shaft 384 has a proximal end 384a fixed to the barrier 380, and a distal end 384b configured to be fixed to and within a trocar 45 (FIG. 10) of the surgical robotic assembly 300. As such, when the barrier 380 of the sterile interface module 306 moves distally toward the trocar 45, in response to a corresponding distal movement of the carriage 304 and the attached instrument drive unit 302 and surgical instrument 400, the tubular shaft 384 collapses along its length. It is contemplated that the tubular shaft 384 may include a plurality of flexible corrugations to allow for the longitudinal expansion and contraction thereof.

Figure 19:
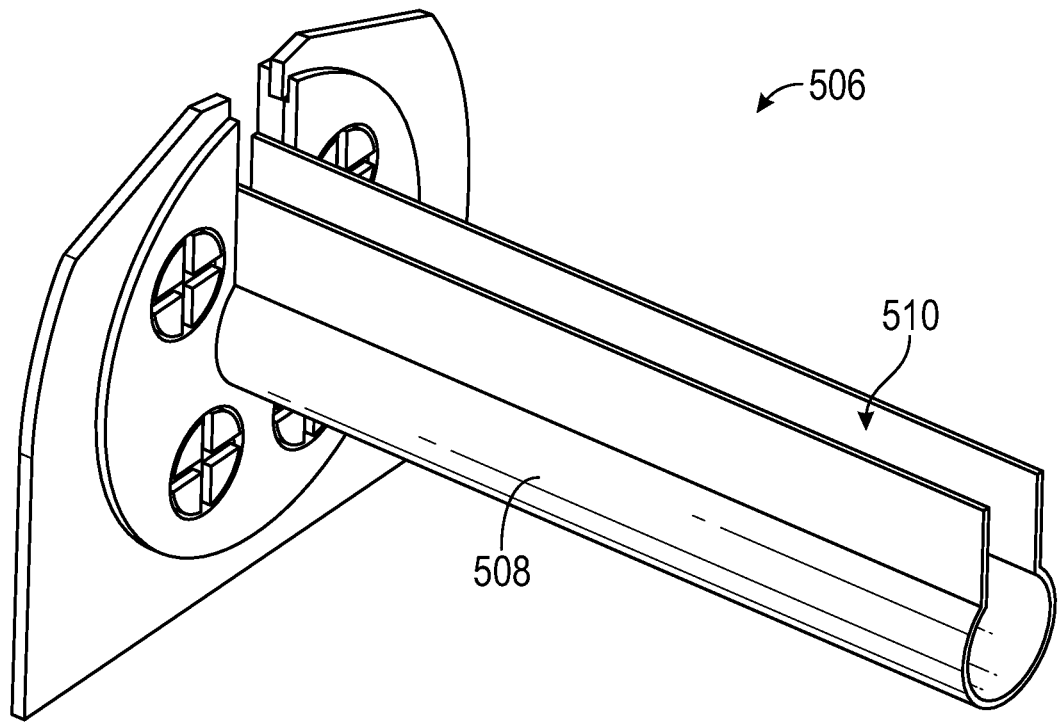
FIG. 19 is a perspective view illustrating another aspect of a sterile interface module for use in the surgical robotic assembly of FIG. 10.

With reference to FIG. 19, another aspect of a sterile interface module 506 is provided, similar to the sterile interface module 306 of FIGS. 17 and 18. However, instead of the tubular shaft 508 being in the form of a collapsible sheath, the tubular shaft 508 of the sterile interface module 506 is rigid along its length and defines a lateral slot 510 along a length thereof that permits for side-loading of the surgical instrument 400 therein.

With reference to FIG. 20, as noted above, the surgical instrument 400 includes the housing 406, the shaft 404 extending distally from the housing 406, and the end effector 402 pivotably coupled to a distal end of the shaft 404. The surgical instrument 400 includes a plurality of driven members 408 each having a driven coupler 410 exposed at a distal end 412 of the housing 406. The driven couplers 410 of the surgical instrument 400 are configured for non-rotational engagement with the corresponding drive couplers 352 (FIG. 12) of the instrument drive unit 302 when the housing 406 of the surgical instrument 400 is positioned on the instrument drive unit 302. When the surgical interface module 306 is used, the barrier 380 of the surgical interface module 306 is positioned between the distal end 412 of the housing 406 of the surgical instrument 400 and the proximal end of the housing 312 of the instrument drive unit 302 whereby the couplers 382 of the sterile interface module 306 couple the driven couplers 410 of the surgical instrument 400 with the corresponding drive couplers 352 of the instrument drive unit 302.

The distal end 412 of the housing 406 of the surgical instrument 400 may have a pair of protrusions 414a, 414b extending distally therefrom configured for receipt in a pair of recesses 390a, 390b (FIG. 18) defined in the barrier 380 of the sterile interface module 306 to provide a mechanical locking of the surgical instrument 400 to the instrument drive unit 302.

It will be understood that various modifications may be made to the aspects disclosed herein. Therefore, the above description should not be construed as limiting, but merely as exemplifications of various aspects. Those skilled in the art will envision other modifications within the scope and spirit of the claims appended thereto.

The invention claimed is:

1. A surgical robotic assembly, comprising:
    a carriage configured for movable engagement to a surgical robotic arm, the carriage having a gear non-rotationally fixed thereto; and
    an instrument drive unit including:
        a housing rotatably supported on the carriage and defining a longitudinal channel configured for passage of a shaft of a surgical instrument;
        a plurality of drive motors supported in the housing and positioned about the longitudinal channel, wherein each drive motor of the plurality of drive motors has a rotatable drive coupler extending proximally from the respective drive motor and configured to interface with a corresponding driven member of the surgical instrument;
        at least one rotation motor having a rotatable coupler configured to be operably coupled to the gear of the carriage such that rotation of the rotatable coupler of the at least one rotation motor rotates the instrument drive unit, including the housing, the plurality of drive motors, and the at least one rotation motor, about a longitudinal axis of the instrument drive unit relative to the carriage; and
        a slip ring assembly coupled to a proximal end portion of the housing of the instrument drive unit, the carriage including an electrical contact in wiping contact with the slip ring assembly to transfer communication signals thereto.

2. The surgical robotic assembly according to claim 1, wherein the gear of the carriage is a ring gear, and the rotatable coupler of the at least one rotation motor is a pinion gear in meshing engagement with the ring gear.

3. The surgical robotic assembly according to claim 2, wherein the instrument drive unit includes an annular guide non-rotationally fixed to the housing of the instrument drive unit and positioned about the longitudinal channel outwardly of the plurality of drive motors, the carriage having at least one bearing interfacing with the annular guide.

4. The surgical robotic assembly according to claim 1, wherein the housing of the instrument drive unit defines a lateral slot extending along a length of the housing and in communication with the longitudinal channel.

5. The surgical robotic assembly according to claim 1, wherein the carriage includes:
    a spine configured for slidable engagement with the surgical robotic arm; and
    a platform extending laterally from the spine and configured to support the housing of the instrument drive unit thereon.

6. The surgical robotic assembly according to claim 5, further comprising a sterile interface module including:
    a barrier rotatably supported on the platform and non-rotationally fixed to the housing of the instrument drive unit;
    a plurality of couplers rotatably supported by the barrier and configured to non-rotatably couple the respective driven member of the surgical instrument to the drive coupler of the instrument drive unit; and
    a tubular shaft extending distally from the barrier and through the longitudinal channel of the instrument drive unit.

7. The surgical robotic assembly according to claim 6, wherein the tubular shaft is a collapsible sheath configured to collapse from a first length to a second, reduced length.

8. The surgical robotic assembly according to claim 1, wherein the housing of the instrument drive unit has an outer surface defining a plurality of longitudinal grooves configured to dissipate heat from the plurality of drive motors.

9. A surgical robotic assembly, comprising:
    an instrument drive unit including:
        a housing defining a longitudinal channel configured for passage of a shaft of a surgical instrument, and a lateral slot extending alongside the longitudinal channel and in communication with the longitudinal channel;
        a plurality of drive motors supported in the housing and positioned about the longitudinal channel, wherein each drive motor of the plurality of drive motors has a rotatable drive coupler configured to interface with a corresponding driven member of the surgical instrument; and
        at least one rotation motor having a rotatable gear, wherein the instrument drive unit, including the housing, the plurality of drive motors, and the at least one rotation motor, are configured to rotate about a longitudinal axis of the instrument drive unit in response to a rotation of the rotatable gear; and
    a sterile interface module including:
        a barrier non-rotationally fixed to the housing of the instrument drive unit;
        a plurality of couplers rotatably supported by the barrier and configured to non-rotatably couple the respective driven member of the surgical instrument to the respective drive coupler of the instrument drive unit; and
        a tubular shaft extending distally from the barrier, the tubular shaft being configured to extend through the longitudinal channel of the instrument drive unit and for passage of the shaft of the surgical instrument.

10. The surgical robotic assembly according to claim 9, wherein the tubular shaft is a collapsible sheath configured to collapse from a first length to a second, reduced length.

11. The surgical robotic assembly according to claim 9, wherein the instrument drive unit includes an annular guide non-rotationally fixed to the housing of the instrument drive unit and positioned about the longitudinal channel outwardly of the plurality of drive motors.

12. The surgical robotic assembly according to claim 9, wherein the housing of the instrument drive unit has an outer surface defining a plurality of longitudinal grooves configured to dissipate heat from the plurality of drive motors.

13. The surgical robotic assembly according to claim 9, wherein the instrument drive unit includes a slip ring assembly coupled to a proximal end portion of the housing of the instrument drive unit.

14. A surgical robotic assembly, comprising:
   a surgical instrument including:
      a housing having a plurality of driven members rotatably supported therein, each of the plurality of driven members having a driven coupler positioned at a distal end of the housing; and
      a shaft extending distally from the housing;
   an instrument drive unit including:
      a housing configured to support the housing of the surgical instrument thereon and defining a longitudinal channel configured for passage of the shaft of the surgical instrument; and
      a plurality of drive motors supported in the housing of the instrument drive unit and positioned about the longitudinal channel, wherein each drive motor of the plurality of drive motors has a rotatable drive coupler positioned at a proximal end of the instrument drive unit and configured to interface with the respective driven coupler of the surgical instrument, wherein the instrument drive unit, including the housing and the plurality of drive motors thereof, are configured to rotate about a longitudinal axis of the instrument drive unit to rotate the surgical instrument about a longitudinal axis of the surgical instrument; and
   a carriage including:
      a spine configured for slidable engagement with a surgical robotic arm; and
      a platform extending laterally from the spine and configured to rotatably support the housing of the surgical instrument and the housing of the instrument drive unit.

15. The surgical robotic assembly according to claim 14, wherein the instrument drive unit includes at least one rotation motor having a rotatable coupler, the instrument drive unit and the surgical instrument being configured to rotate about the respective longitudinal axes thereof in response to a rotation of the rotatable coupler.

16. The surgical robotic assembly according to claim 15, further comprising a carriage configured for movable engagement to a surgical robotic arm, the carriage having a gear non-rotationally fixed thereto and configured for operable engagement with the rotatable coupler.

17. The surgical robotic assembly according to claim 16, wherein the gear of the carriage is a ring gear, the rotatable coupler of the at least one rotation motor being a pinion gear in meshing engagement with the ring gear.

18. The surgical robotic assembly according to claim 14, wherein the instrument drive unit includes an annular guide non-rotationally fixed to the housing of the instrument drive unit and positioned about the longitudinal channel outwardly of the plurality of drive motors, the carriage having at least one bearing interfacing with the annular guide.

* * * * *